(12) United States Patent
Slupsky et al.

(10) Patent No.: US 8,685,739 B2
(45) Date of Patent: Apr. 1, 2014

(54) URINE BASED DETECTION OF A DISEASE STATE CAUSED BY A PNEUMOCOCCAL INFECTION

(75) Inventors: Carolyn Slupsky, Davis, CA (US); Thomas Marrie, Chester Basin (CA)

(73) Assignee: Carolyn Slupsky, Davis, CA (US)

( * ) Notice: Subject to any disclaimer, the term of this patent is extended or adjusted under 35 U.S.C. 154(b) by 346 days.

(21) Appl. No.: 12/595,610

(22) PCT Filed: Apr. 14, 2008

(86) PCT No.: PCT/CA2008/000670
§ 371 (c)(1),
(2), (4) Date: Jan. 22, 2010

(87) PCT Pub. No.: WO2008/124920
PCT Pub. Date: Oct. 23, 2008

(65) Prior Publication Data
US 2010/0136600 A1      Jun. 3, 2010

Related U.S. Application Data

(60) Provisional application No. 60/907,638, filed on Apr. 12, 2007.

(51) Int. Cl.
*G01N 33/48* (2006.01)
*C12Q 1/02* (2006.01)
*C12Q 1/70* (2006.01)

(52) U.S. Cl.
USPC ................ 436/63; 436/86; 436/89; 436/95; 436/96; 436/111; 436/128; 436/130; 436/131; 436/161; 436/173; 435/5; 435/29

(58) Field of Classification Search
USPC ........... 436/14, 63, 86, 89, 95, 161, 164, 171, 436/173, 128, 96, 111, 130, 131; 435/4, 5, 435/14, 29, 36; 702/19
See application file for complete search history.

(56) References Cited

U.S. PATENT DOCUMENTS

| | | |
|---|---|---|
| 7,181,348 B2 | 2/2007 | Wishart |
| 7,191,069 B2 | 3/2007 | Wishart |
| 2005/0130321 A1* | 6/2005 | Nicholson et al. ............ 436/518 |
| 2005/0148039 A1* | 7/2005 | Moore et al. ................. 435/7.32 |
| 2006/0293859 A1 | 12/2006 | Pipke |
| 2007/0015172 A1* | 1/2007 | Zhang et al. ...................... 435/6 |
| 2009/0130775 A1 | 5/2009 | Fujiwara |
| 2010/0047799 A1* | 2/2010 | Badwan et al. .................... 435/6 |
| 2010/0227341 A1* | 9/2010 | Briles et al. ................... 435/7.92 |

FOREIGN PATENT DOCUMENTS

| | | |
|---|---|---|
| WO | 03/005628 A2 | 1/2003 |
| WO | 2006/118004 A1 | 11/2006 |
| WO | 2008/022299 A1 | 2/2008 |

OTHER PUBLICATIONS

Webster's Ninth New Collegiate Dictionary, 1990, p. 46.*
Brandenburg, J.A., et al., "Clinical Presentation, Processes and Outcomes of Care for Patients with *Pneumococcal pneumonia*," J Gen Intern Med 15:638-646, Sep. 2000.
Braun, J.S., et al., "Pneumolysin Causes Neuronal Cell Death through Mitochondrial Damage," American Society for Microbiology: Infection and Immunity 75(9):4245-4254, Sep. 2007.
Centers for Disease Control and Prevention, "Defining the Public Health Impact of the Drug Resistant *Streptococcus pneumoniae*: Report of a Working Group," MMWR Morbid Mortal Weekly Report 45(RR-I):1-14, Feb. 1996.
Cunha, B.A., "Community-Acquired Pneumonia Diagnostic and Therapeutic Approach," Medical Clinics of North America 85(1):43-77, Jan. 2001.
Cunha, B.A., "*Nosocomial pneumonia* Diagnostic and Therapeutic Considerations," Medical Clinics of North America 85(1):79-114, Jan. 2001.
Faden, H., "Urinary Excretion of Pneumococcal Cell Wall Polysaccharide in Children," The Pediatric Infectious Disease Journal 21(8):791-793, Aug. 2002.
Fine, M.J., et al., "Prognosis and Outcomes of Patients with Community-Acquired Pneumonia," A Meta-Analysis: JAMA 275(2):134-141, Jan. 1996.
Hoskins, J., et al., "Genome of the Bacterium *Streptococcus pneumoniae* Strain R6," American Society of Microbiology: Journal of Bacteriology 183(19):5709-5717, Oct. 2001.
Kasper, D.L., et al., "Harrison's Principles of Internal Medicine," 16d ed., Mc-Graw-Hill Professional, Blacklick, OH, 2006, p. 1537.

(Continued)

*Primary Examiner* — Maureen Wallenhorst
(74) *Attorney, Agent, or Firm* — Christensen O'Connor Johnson Kindness PLLC

(57) ABSTRACT

There is provided a method of diagnosing a disease state in a subject. The disease state is caused or effected by pneumococcal infection. The method includes obtaining a biological test sample from the subject. The biological sample includes at least one metabolite selected from the group consisting of citrate, trigonelline, acetylcarnitine, acetone, myo-inositol, 3-hydroxybutyrate, glucose and carnitine. A respective concentration of each one of the at least one metabolite is compared with a predetermined concentration value associated with a corresponding one of the at least one metabolite. The predetermined concentration value is indicative of the disease state. For example, the biological sample includes any one of citrate, trigonelline, acetylcarnitine, acetone, myoinositol, 3-hydroxybutyrate, glucose and carnitine. As a further example, the biological samples include any combination of citrate, trigonelline, acetylcarnitine, acetone, myo-inositol, 3-hydroxybutyrate, glucose and carnitine. As a further example, the biological sample includes each one of citrate, trigonelline, acetylcarnitine, acetone, myoinositol, 3-hydroxybutyrate, glucose and carnitine.

32 Claims, 12 Drawing Sheets

(56) References Cited

OTHER PUBLICATIONS

Leverve, X.M., "Mitochondrial Function and Substrate Availability," The Society of Critical Care Medicine and Lippincott Williams & Wilkins 35(9):S454-S460, Sep. 2007.

Lindon, J.C., et al., "Metabonomics Technologies and their Applications in Physiological Monitoring, Drug Safety Assessment and Disease Diagnosis," Biomarkers 9(1):1-31, Jan.-Feb. 2004.

Lindon, J.C., et al., "So what's the Deal with Metabonomics?," Anal Chem 75(17):384A-391A, Sep. 2003.

Marston, B.J., et al., "Incidence of Community-Acquired Pneumonia Requiring Hospitalization," Arch Intern Med 157:1709-1718, Aug. 1997.

Musher, D.M., "Infections Caused by *Streptococcus pneumoniae*: Clinical Spectrum, Pathogenesis, Immunity, and Treatment," Clin Infect Dis 14(4):801-807, Apr. 1992.

Nunes, A.A., et al., "Antigen Detection for the Diagnosis of Pneumonia," Pediatric Pulmonology 38:135-139, May 2004.

Oresic, et al., "Metabolomic Approaches to Phenotype Characterization and Applications to Complex Diseases," Expert Rev. Mol. Diagn. 6(4):575-585, 2006.

Ridgway, E.J., et al., "Capsular Serotypes and Antibiotic Sensitivity of *Streptococcus pneumoniae* Isolated from Primary-School Children," Journal of Infection 30:245-251, 1995.

Slupsky, C.M., et al., "Investigations of the Effects of Gender, Diurnal Variation, and Age in Human Urinary Metabolomic Profiles," Anal. Chem. 79(18):6995-7004, Sep. 2007.

Stulbarg, M., "Problems in Diagnosing Pneumonia," West J Med 140:594-601, Apr. 1984.

Wilson, P.A., and J. Ferguson, "Severe Community-Acquired Pneumoma: an Australian Perspective," Int Med J 35:699-705, 2005.

Chan, E.C.Y., et al., "Metabolic Profiling of Human Colorectal Cancer Using High-Resolution Magic Angle Spinning Nuclear Magnetic Resonance (HR-MAS NMR) Spectroscopy and Gas Chromatography Mass Spectrometry (GC/MS)," Journal of Proteome Research 8(1):352-361, Jan. 2009.

Denkert, C., et al., "Metabolite Profiling of Human Colon Carcinoma—Deregulation of TCA Cycle and Amino Acid Turnover," Molecular Cancer 7:72, Sep. 2008, 15 pages.

Dieterle, F., et al., "Probabilistic Quotient Normalization as Robust Method to Account for Dilution of Complex Biological Mixtures. Application in [1] H NMR Metabonomics," Analytical Chemistry 78(13):4281-4290, Jul. 2006.

Fan, X., et al., "Diagnosis of Breast Cancer Using HPLC Metabonomics Fingerprints Coupled With Computational Methods," Proceedings of the 27th Annual Conference of the IEEE Engineering in Medicine and Biology Society, Shanghai, Sep. 1-4, 2005, pp. 6081-6084.

Frickenschmidt, A., et al., "Metabonomics in Cancer Diagnosis: Mass Spectrometry-Based Profiling of Urinary Nucleosides From Breast Cancer Patients," Biomarkers 13(4):435-449, Jun. 2008.

Ganapathy, V., et al., "Nutrient Transporters in Cancer: Relevance to Warburg Hypothesis and Beyond," Pharmacology & Therapeutics 121(1):29-40, Jan. 2009.

Gao, H., et al., "Application of [1] H NMR-Based Metabonomics in the Study of Metabolic Profiling of Human Hepatocellular Carcinoma and Liver Cirrhosis," Cancer Science 100(4):782-785, Apr. 2009.

Garber, K., "Energy Boost: The Warburg Effect Returns in a New Theory of Cancer," Journal of the National Cancer Institute 96(24):1805-1806, Dec. 2004.

Jordan, K.W., et al., "Metabolomic Characterization of Human Rectal Adenocarcinoma With Intact Tissue Magnetic Resonance Spectroscopy," Diseases of the Colon and Rectum, Author manuscript, Mar. 2010, 14 pages. [Published in final edited form in Diseases of the Colon and Rectum 52(3):520-525, Mar. 2009].

Kim, K., et al., "Urine Metabolomics Analysis for Kidney Cancer Detection and Biomarker Discovery," Molecular & Cellular Proteomics 8(3):558-570, Mar. 2009.

Mahadevan, S., et al., "Analysis of Metabolomic Data Using Support Vector Machines," Analytical Chemistry 80(19):7562-7570, Oct. 2008.

Moss, E.L, et al., "The Role of CA125 in Clinical Practice," Journal of Clinical Pathology 58(3):308-312, Mar. 2005.

Murdoch, T.B., "Urinary Metabolic Profiles of Inflammatory Bowel Disease in Interleukin-10 Gene-Deficient Mice," Analytical Chemistry 80(14):5524-5531, Jul. 2008.

Nyström, L., et al., "Breast Cancer Screening With Mammography: Overview of Swedish Randomised Trials," Lancet 341(8851):973-978, Apr. 1993.

Qiu, Y., et al., "Urinary Metabonomic Study on Colorectal Cancer," Journal of Proteome Research 9(3):1627-1634, Mar. 2010.

Skaane, P., "Studies Comparing Screen-Film Mammography and Full-Field Digital Mammography in Breast Cancer Screening: Updated Review," Acta Radiologica 50(1):3-14, Jan. 2009.

Slupsky, C.M., et al., "*Pneumococcal pneumonia*: Potential for Diagnosis Through a Urinary Metabolic Profile," Journal of Proteome Research 8(12):5550-5558, Dec. 2009.

Slupsky, C.M., et al., "*Streptococcus pneumoniae* and *Staphylococcus aureus* Pneumonia Induce Distinct Metabolic Responses," Journal of Proteome Research 8(6):3029-3036, Jun. 2009.

Tiziani, S., et al., "Early Stage Diagnosis of Oral Cancer Using [1] H NMR-Based Metabolomics," Neoplasia 11(3):269-276, 4 additional pages, Mar. 2009.

Weljie, A.M., et al., "Targeted Profiling: Quantitative Analysis of [1] H NMR Metabolomics Data," Analytical Chemistry 78(13):4430-4442, Jul. 2006.

Woo, H.M., et al., "Mass Spectrometry Based Metabolomic Approaches in Urinary Biomarker Study of Women's Cancers," Clinica Chimica Acta 400(1-2):63-69, Feb. 2009.

* cited by examiner

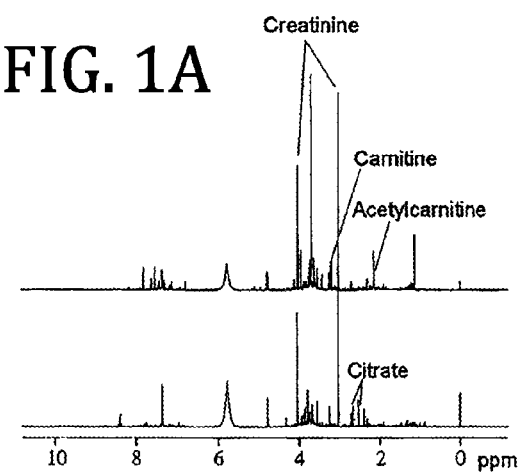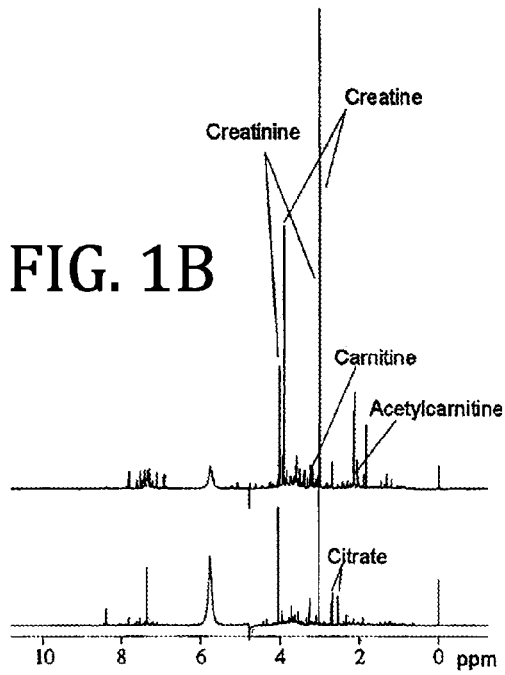
FIG. 1A　　FIG. 1B
FIG. 1C　　FIG. 1D

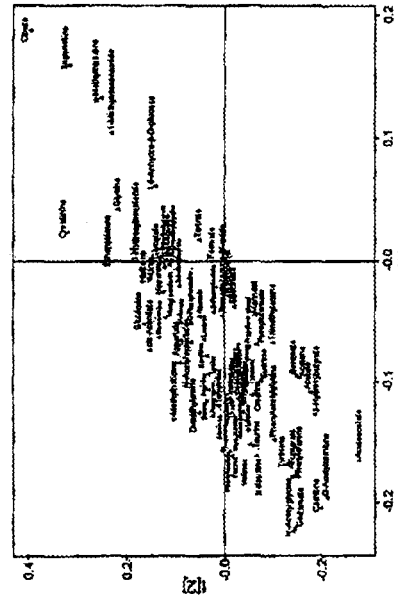
FIG. 3.1B
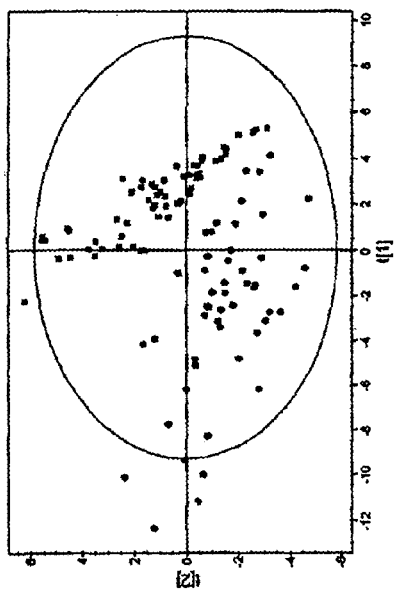
FIG. 3.1A
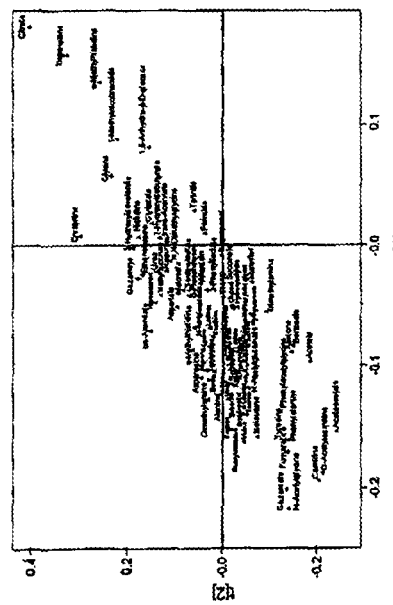
FIG. 3.1D
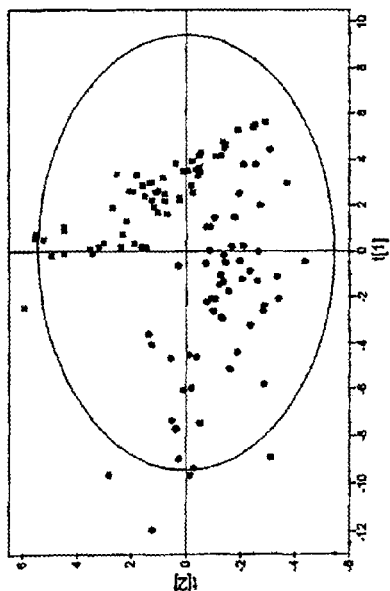
FIG. 3.1C

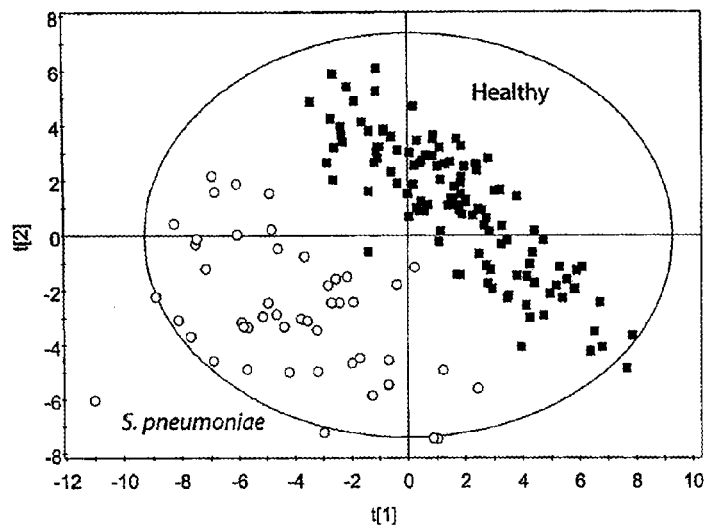
FIG. 3.2A
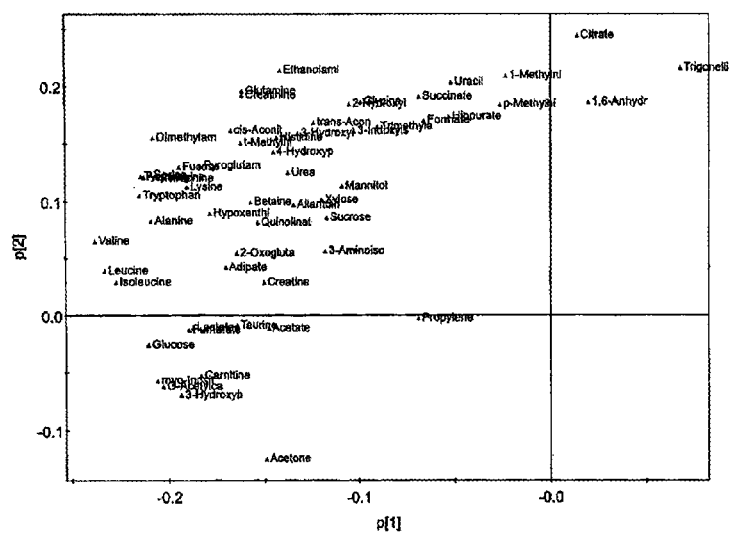
FIG. 3.2B

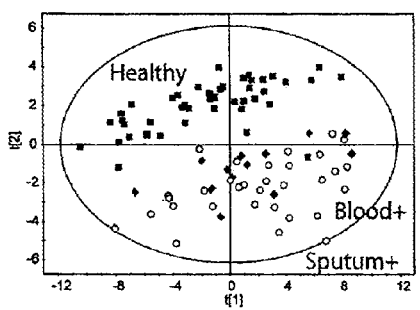
FIG. 5A
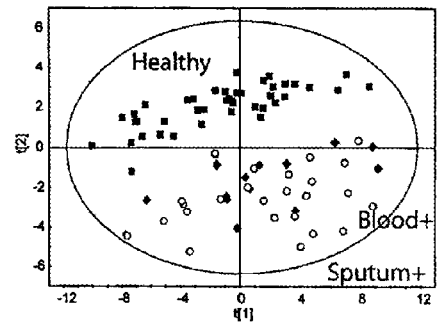
FIG. 5B
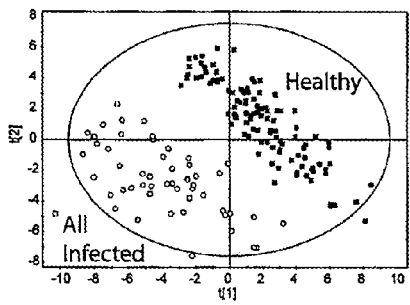
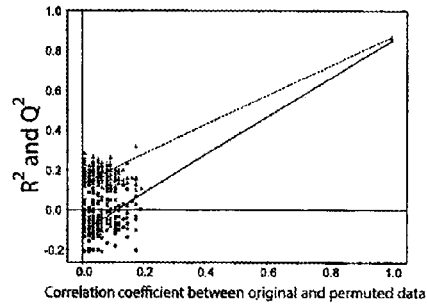
FIG. 5C
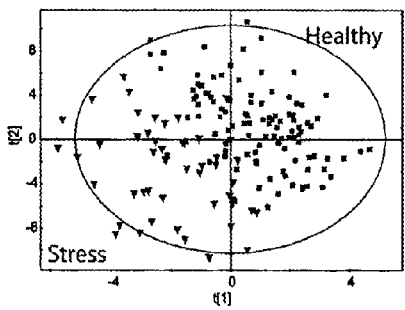
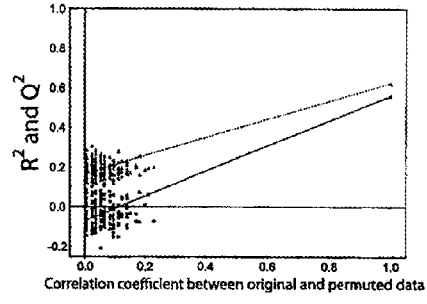
FIG. 5D
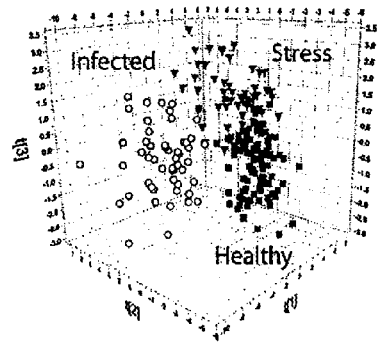
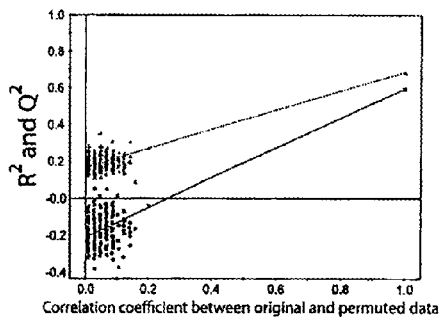
FIG. 5E

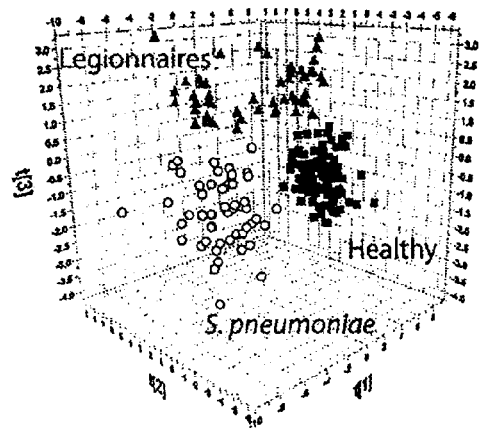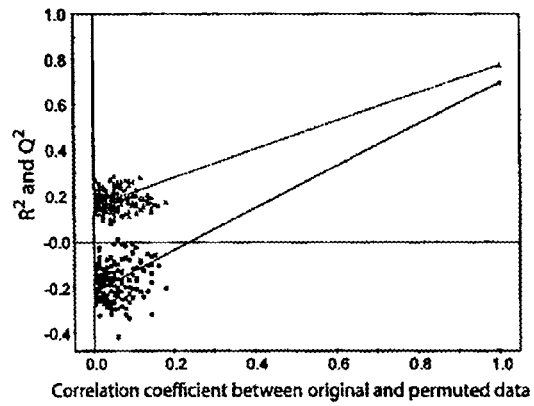
FIG. 9A
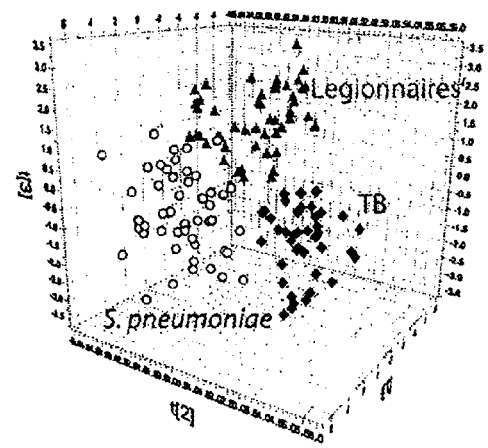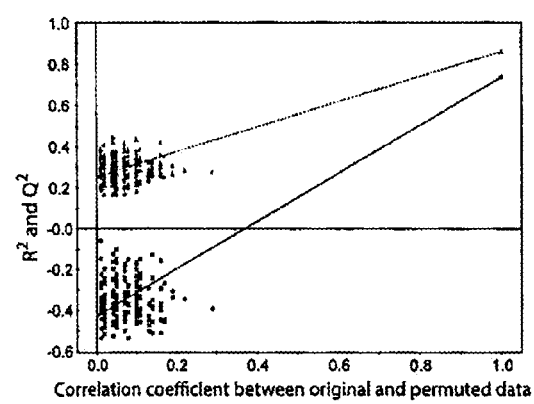
FIG. 9B

| Table 1: Demographics of false negative and false positive patients from blinded study. | | | | | | | | | |
|---|---|---|---|---|---|---|---|---|---|
| | Patient | Age | Gender | Culture | X-ray | Diagnosis | CR$_{bl}$ | CR$_{ur}$ | Meds | Comorbidities |
| False Neg. | 1 | 50 | F | + | + | BPP | 92 | 6.9 | n/a | HIV |
| | 2 | 70 | M | + | + | BPP | 72 | 1.7 | Citalopram, lorazepam, glyburide, clonazepam, prednisone, diltiazem, cyclophos, percocet, ipratropium, salbutamol, ventolin, ranitidine, gatifloxacin, ASA, senokot | Multiple myeloma / diabetes |
| | 3 | 89 | M | + | + | n/a | n/a | 13.6 | n/a | n/a |
| | 4 | 32 | M | + | + | BPP | 101 | 6.6 | Advil / celexa / dimetapp | asthma |
| | 5 | 26 | F | + | + | BPP | 85 | 20.7 | Moxifloxacin, percocet, ketorolac, gravol | Mild asthma |
| False Pos. | 1 | 45 | F | - | - | Laceration | 82 | 6.2 | Anti-hypertensive drugs / vitamins | n/a |
| | 2 | 58 | M | - | + | CHF | 113 | 1.6 | ACE inhibitors, antiplatelet, beta blockers, diuretics, insulin, oral hypoglycemic agent, statins, losec | Diabetes / ischemic heart disease |
| | 3 | 65 | F | n/a | - | COPD | n/a | 5.6 | Steroids / Abx | n/a |
| | 4 | 59 | M | n/a | + | TB | n/a | 14.4 | Eth / Inh / Pyr / B6 / rifampin | COPD / Heart Disease |
| | 5 | 30 | M | n/a | + | TB | n/a | 11.9 | Eth / Inh / Pyr / B6 / rifampin | HIV |
| | 6 | 27 | F | n/a | + | TB | n/a | 3.6 | Eth / Inh / Pyr / B6 / rifampin | none |
| | 7 | 45 | F | n/a | + | TB | n/a | 16.5 | Eth / Inh / Pyr / B6 / rifampin | Substance abuse |

Culture "+" - positive blood culture; Culture "-" – negative blood culture; X-ray "+" - consolidation on radiograph; X-ray "-" – no consolidation on radiograph; Cr$_{bl}$ – blood creatinine (μM); Cr$_{ur}$ – urine creatinine (mM); n/a – not available; cyclophos – cyclophosphamide; Eth – ethambutol; INH – isoniazid; Pyr – pyrazinamide; B6 – vitamin B6; Abx – antibiotic (unknown);

FIG. 11

URINE BASED DETECTION OF A DISEASE STATE CAUSED BY A PNEUMOCOCCAL INFECTION

FIELD OF THE INVENTION

The present invention pertains to the field of diagnosis of a disease state.

BACKGROUND OF THE INVENTION

A disease state, caused or effected by a pneumococcal infection, is often difficult to diagnose.

Pneumonia is an acute, occasionally chronic, infection of the lower respiratory tract caused by a variety of pathogens including bacteria, viruses, fungi and parasites[1,2]. A variety of non-infectious processes such as congestive heart failure, pulmonary infarction, vasculitis, and drug reactions can mimic pneumonia[3]. Despite progress in the development of antibiotics, diagnostic imaging, and critical care medicine, pneumonia remains the leading cause of death from infection in North America mainly because of the difficulty in promptly identifying the etiologic agent[4,5]. In practice, leas than 20% of patients admitted to hospital with pneumonia obtain an etiological diagnosis[4,6].

*Streptococcus pneumoniae*, the major causative pathogen of pneumonia[7], is a transient commensal organism of the throat and upper respiratory tract[8] in ~40% of the population. However, *S. pneumoniae* frequently becomes virulent, especially for those at the extremes of age, immunocompromised individuals, those with chronic diseases, and tobacco smokers[6]. Each year, millions of people in the United States are infected resulting in 500,000 hospitalizations[9]. Indeed, invasive *S. pneumoniae* is a leading cause of death worldwide, with a mortality rate of up to 25%[10].

Currently, diagnosis of a disease state effected by or caused by an infectious lung disease, such as pneumococcal pneumonia, is made by positive blood or sputum culture (pleural fluid or material obtained by bronchoalveolar lavage (BAL) may also be cultured) in the presence of a compatible clinical picture. Blood and sputum cultures yield *S. pneumoniae* in 6-10% and 11% of patients respectively[11]. Moreover, results are rarely available within 36 hours, and a positive sputum culture for *S. pneumoniae* only indicates that this pathogen is possible or at best a probable cause of pneumonia[9]. To combat lengthy diagnostic times, other tests have been developed such as the NOW test (Binax Inc.) which detects cell wall polysaccharide of *S. pneumoniae* in urine. However, this test is positive for only about 80-90% of bacteremic patients[12]. Since no gold standard test exists for those disposed in a disease state effected or caused by an infectious lung disease, such as non-bacteremic pneumococcal pneumonia, we do not know whether this test has value. Furthermore, a 65% false positive rate is seen with this test in children who carry this microorganism asymptomatically in their nasopharynx[12].

An ideal diagnostic tool for the disease state effected or caused by an infectious lung disease such as *S. pneumoniae* infection, would be one that is non-invasive, requires a minimal amount sample not contaminated by carriage of the organism from the site at which it was obtained, can be done quickly with high sensitivity and specificity, is technically simple to carry out, and ideally inexpensive.

Metabolomics is an emerging science dedicated to the global study of metabolites; their composition, interactions, dynamics, and responses to disease or environmental changes in cells, tissues and biofluids. While the idea of using metabolomics for diagnostic purposes is not new, technology has changed significantly and sufficiently to allow the simultaneous measurement of literally hundreds of metabolites at once. A number of metabolomics studies have reported differences between disease and healthy states and these have been previously reviewed[13-15].

SUMMARY OF THE INVENTION

In one aspect, there is provided a method of diagnosing a disease state in a subject. The disease state is caused or effected by a pneumococcal infection. The method includes obtaining a biological test sample from the subject. The biological sample includes at least one metabolite selected from the group consisting of citrate, trigonelline, acetylcarnitine, acetone, myo-inositol, 3-hydroxybutyrate, glucose and carnitine. The respective concentration of each one of the at least one metabolite is determined. The profile for the biological test sample using at least the respective concentration of each one of the at least one metabolite is determined. The profile of the biological test sample is compared with a predetermined profile indicative of the disease state. For example, the biological sample includes any one of citrate, trigonelline, acetylcarnitine, acetone, myo-inositol, 3-hydroxybutyrate, glucose and carnitine. As a further example, the biological sample includes any combination of citrate, trigonelline, acetylcarnitine, acetone, myo-inositol, 3-hydroxybutyrate, glucose and carnitine. As a further example, the biological sample includes each one of citrate, trigonelline, acetylcarnitine, acetone, myo-inositol, 3-hydroxybutyrate, glucose and carnitine.

In another aspect, there is provided a method of diagnosing a disease state in a subject. The disease state is caused or effected by a pneumococcal infection. The method includes obtaining a biological test sample from the subject. The biological sample includes at least one metabolite selected from the group consisting of citrate, trigonelline, acetylcarnitine, acetone, myo-inositol, 3-hydroxybutyrate, glucose and carnitine. A respective concentration of each one of the at least one metabolite is compared with a predetermined concentration value associated with a corresponding one of the at least one metabolite, such that at least one predetermined concentration value is being compared, and wherein the at least one predetermined concentration value is indicative of the disease state. For example, the biological sample includes any one of citrate, trigonelline, acetylcarnitine, acetone, myo-inositol, 3-hydroxybutyrate, glucose and carnitine. As a further example, the biological samples include any combination of citrate, trigonelline, acetylcarnitine, acetone, myo-inositol, 3-hydroxybutyrate, glucose and carnitine. As a further example, the biological sample includes each one of citrate, trigonelline, acetylcarnitine, acetone, myo-inositol, 3-hydroxybutyrate, glucose and carnitine.

In yet another aspect, there is provided a method of diagnosing a disease state in a subject. The disease state is caused or effected by a pneumococcal infection. The method includes obtaining a biological test sample from the subject. The biological sample includes at least one metabolite selected from the group consisting of citrate, succinate 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, swine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. The respective concentration of each one of the at least one metabolite is determined. The profile for the biological test sample using at least the respective concentration of each one of the at least one metabolite is determined. The profile of the biological test sample is compared with a predetermined profile indicative of the disease state. For example, the biological sample includes any one of citrate, geminate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological samples include any combination of citrate, succinate, 1-methylnicotinamide, levoglucosan, trigonelline, hippurate, glycine, ethanolamine, uracil, dimethylglycine, guanidoacetate, glycolate; π-methylhistidine, alanine, asparagine, isoleucine, leucine; lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological sample includes each one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, sake, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate.

In a further aspect, there is provided a method of diagnosing a disease state in a subject. The disease state is caused by a pneumococcal inaction. The method includes obtaining a biological test sample from the subject. The biological sample includes at least out metabolite selected from the group consisting of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creating, 2-oxoglutarate and fumarate. A respective concentration of each one of the at least one metabolite is compared with a predetermined concentration value associated with a corresponding one of the at least one metabolite, such that at least one predetermined concentration value is being compared, and wherein the at least one predetermined concentration value is indicative of the disease state. For example, the biological sample includes any one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological samples include any combination of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, marine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological sample includes each one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate.

In another aspect, the quantities of the compounds are detected through use of an antibody preferentially reactive with the compounds, said antibody detected through colormetric or radiometric means otherwise known in the art. In a further embodiment, the compounds are detected through use of a human or machine readable strip, in which the presence of said compounds, relative to a control, is detectable through a colormetric change in said human or machine readable strip via a chemical reaction between a compound present in or on said human or machine readable strip and at least one of said compounds. In a further embodiment, the compounds are detected through use of a human or machine readable strip, in which the presence of said compounds, relative to a control, is detectable through a colormetric change in said human or machine readable strip via a chemical reaction between a compound present in or on said human or machine readable strip and at least one other molecule wherein at least one of said at least one other molecule interacts preferentially with at least one said of compounds.

The accompanying description illustrates preferred embodiments of the present invention and serves to explain the principles of the present invention.

BRIEF DESCRIPTION OF THE DRAWINGS

FIG. 1 shows the 600 MHz 1H NMR spectra obtained from (A) 26 year-old male with a possible case of pneumococcal pneumonia, (B) 58 year-old female with bacteremic pneumococcal pneumonia, (C) Healthy 26 year-old male, (D) Healthy 57 year-old female. None of these patients had diabetes.

FIG. 3.1 shows PLS-DA analyses of the (A) metabolite concentrations determined from the 1H NMR spectra obtained from all 59 pneumococcal patients and 59 healthy controls, (B) metabolite concentrations determined from the 1H NMR spectra obtained from 50 non-diabetic pneumococcal patients (removal of the 9 diabetic patient data) and 59 healthy controls. (C) Loadings plot corresponding to (A). (D) Loadings plot corresponding to (B). Controls, squares; pneumococcal patients, circles. Concentration data identified in Table 2 for each one "guanidoacetate or unknown", "glycolate or unknown", "2-aminobutyrate or unknown", "isopropanol or unknown", "pyruvate or unknown", "tartrate or unknown", is assigned to the respective one of guanidoacetate, glycolate, 2-aminobutyrate, isopropanol, pyruvate, and tartrate.

FIG. 3.2 shows PLS-DA analyses of the (A) metabolite concentrations determined from the 1H NMR spectra obtained from all 59 pneumococcal patients and 59 healthy controls, (B) Loadings plot corresponding to (A). Controls, squares; pneumococcal patients, circles.

FIG. 5: a, PCA model (based on 61 measured metabolites) of age- and gender-matched "healthy" subjects versus those with pneumococcal pneumonia. "Healthy" subjects (■, n=47); bacteremic pneumococcal pneumonia (○, n32); sputum or endotracheal tube positive *S. pneumoniae* cultures (♦, n=15). b, PCA model as in a with removal of diabetics (8 pneumonia patients, and 3 "healthy" subjects). c, PLS-DA model and validation (using 200 permutations) based on 61 measured metabolites using all "healthy" subjects and *S. pneumoniae* patients (n=52 for *S. pneumoniae* group (○); n=115 for healthy group (■)). d, PLS-DA model and validation (using 200 permutations) based on 61 measured metabolites of non-infectious metabolic stress (n=57 (♦)), and healthy (n=115 (■)). e, 3D PLS-DA model and validation (using 200 permutations) of all three groups (*S. pneumoniae* (○), non-infectious metabolic stress (♦), and healthy (■)).

FIG. 9: a, PLS-DA model and validation (using 200 permutations) based on 61 measured metabolites (n=52 for *S. pneumonia* group (○); n=115 for healthy group (■), n=74 for *L. pneumophila* group (▲)). b, PLS-DA model and validation (using 200 permutations) based on 61 measured metabolites (n=52 for *S. pneumoniae* group (○); n=74 for *L. pneumophila* group (▲), n=52 for *M. tuberculosis* group (♦)).

FIG. 11 summarizes the characteristics of false negatives and false positives for the Blinded Study in Example 2.

DETAILED DESCRIPTION OF THE PRESENT INVENTION

Figure 2:
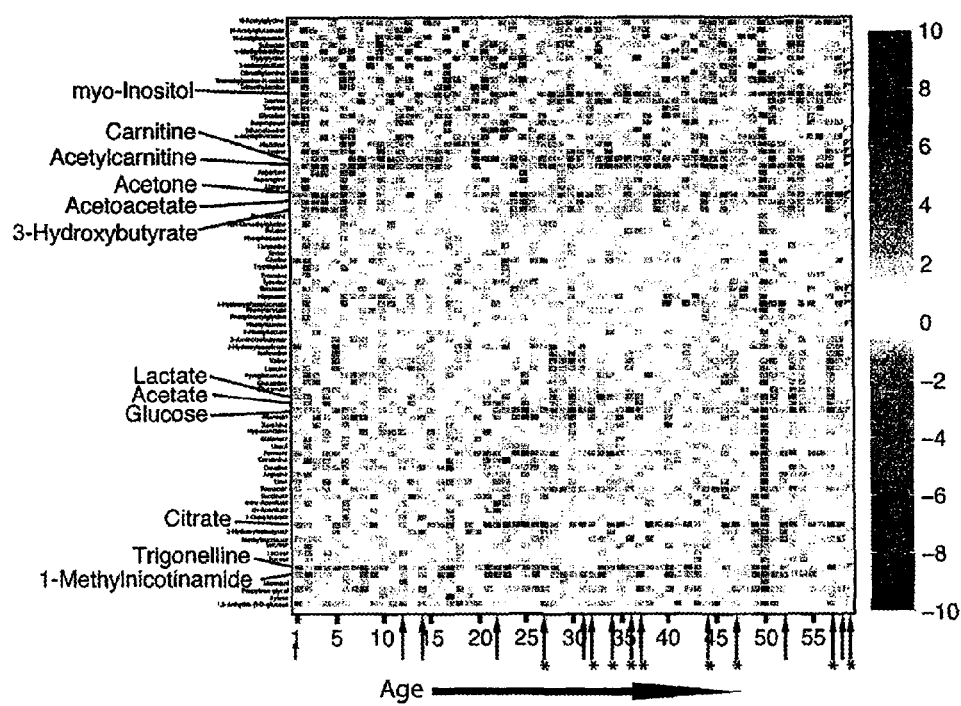
FIG. 2 shows a HEAT Map Representation of metabolite concentrations for pneumococcal patients. Each value was obtained after log-transformation by subtracting the average metabolite concentration determined from the control population from the pneumococcal patient metabolite concentration and dividing by the standard deviation of the control population. The coloring/shading, representing the magnitude of the deviation, is shown as a side-bar. Those patients who died as a result of complications due to pneumococcal disease are indicated by the arrows. Those patients who had diabetes are indicated by the asterisk. The patients are ordered from youngest (patient 1, 6 days old) to oldest (patient 59, 92 years old).

In one embodiment, there is provided a method of diagnosing a disease state in a subject. For example, the subject is a human subject. The disease state is caused or effected by a pneumococcal infection. For example, the disease state is caused by *streptococcus pneumoniae*. The method includes obtaining a biological test sample from the subject. The biological sample includes at least one metabolite selected from the soup consisting of citrate, trigonelline, acetylcarnitine, acetone, myo-inositol, 3-hydroxybutyrate, glucose and carnitine. The respective concentration of each one of the at least one metabolite is determined. The profile for the biological test sample using at least the respective concentration of each one of the at least one metabolite is determined. The profile of the biological test sample is compared with a predetermined profile indicative of the disease state. For example, the biological sample includes any one of citrate, trigonelline, acetylcarnitine, acetone, myo-inositol, 3-hydroxybutyrate, glucose and carnitine. As a further example, the biological sample includes any combination of citrate, trigonelline, acetylcarnitine, acetone, myo-inositol, 3-hydroxybutyrate, glucose and carnitine. As a further example, the biological sample includes each one of citrate, trigonelline, acetylcarnitine, acetone, myo-inositol, 3-hydroxybutyrate, glucose and carnitine.

In another embodiment, there is provided a method of diagnosing a disease state in a subject. For example, the subject is a human subject. The disease state is caused or effected by a pneumococcal infection. For example, the disease state is caused by *streptococcus pneumoniae*. The method includes obtaining a biological test sample from the subject. The biological sample includes at least one metabolite selected from the group consisting of citrate, trigonelline, acetylcarnitine, acetone, myo-inositol, 3-hydroxybutyrate, glucose and carnitine. A respective concentration of each one of the at least one metabolite is compared with a predetermined concentration value associated with a corresponding one of the at least one metabolite, such that at least one predetermined concentration value is being compared, and wherein the at least one predetermined concentration value is indicative of the disease state. For example, the biological sample includes any one of citrate, trigonelline, acetylcarnitine, acetone, myoinositol, 3-hydroxybutyrate, glucose and carnitine. As a further example, the biological samples include any combination of citrate, trigonelline, acetylcarnitine, acetone, myo-inositol, 3-hydroxybutyrate, glucose and carnitine. As a further example, the biological sample includes each one of citrate, trigonelline, acetylcarnitine, acetone, myo-inositol, 3-hydroxybutyrate, glucose and carnitine.

In another embodiment, there is provided a method of diagnosing a disease state in a subject. For example, the subject is a human subject. The disease state is caused or effected by a pneumococcal infection. For example, the disease state is caused by *streptococcus pneumoniae*. The method includes obtaining a biological test sample from the subject. The biological sample includes at least one metabolite selected from the group consisting of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutylate, acetone, carnitine, acetylcarnitine, hypoxanthine, fucose, myo-inositol, taurine, creatine, 2-oxoglutarate and fumarate.

The respective concentration of each one of the at least one metabolite is determined. The profile for the biological test sample using at least the respective concentration of each one of the at least one metabolite is determined. The profile of the biological test sample is compared with a predetermined profile indicative of the disease state. For example, the biological sample includes any one of citrate, succinate, 1-methylnicotinamide, levoglucosan, hippurate, glycine, ethanolamine, uracil, dimethylglycine, guanidoacetate, glycolate, π-methylhistidine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological samples include any combination of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological sample includes each one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate.

In another embodiment, there is provided a method of diagnosing a disease state in a subject. For example, the subject is a human subject. The disease state is caused or effected by a pneumococcal infection. For example, the disease state is caused by *streptococcus pneumoniae*. The method includes obtaining a biological test sample from the subject. The biological sample includes at least one metabolite selected from the soup consisting of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. A respective concentration of each one of the at least one metabolite is compared with a predetermined concentration value associated with a corresponding one of the at least one metabolite, such that at least one predetermined concentration value is being compared, and wherein the at least one predetermined concentration value is indicative of the disease state. For example, the biological sample includes any one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological samples include any combination of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate. As a further example, the biological sample includes each one of citrate, succinate, 1-methylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, hydroxybutyrate, acetone, carnitine, acetylcarnitine, hypoxanthine, fucose, myo-inositol, taurine, creatine, 2-oxoglutarate and fumarate.

Each one of the terms "concentration" and "concentration value" is a concentration or a numerical value associated with or derived from a concentration, including a numerical value resulting from a statistical analysis of a concentration or a numerical value associated with or derived from a concentration.

"Metabolites" include, but are not limited to, lipids, steroids, amino acids, organic acids, bile acids, eicosanoids, and peptides.

For example, with respect to the biological test sample, the biological test sample is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, or sputum. For example, the biological test sample is urine.

For example, with respect to the concentration of a metabolite, the concentration of a metabolite is determined using a spectrometric technique. Examples of suitable spectrometric techniques includes liquid chromatography, gas chromatography, liquid chromatography-mass spectrometry, gas chromatography-mass spectrometry, high performance liquid chromatography-mass spectrometry, capillary electrophoresis-mass spectrometry, nuclear magnetic resonance spectrometry, roman spectroscopy, or near infrared spectroscopy. For example, the determination is made using nuclear magnetic resonance spectrometry.

For example, with respect to the profile of the biological test sample, the profile is determined by performing a statistical analysis using at least the respective concentration of each one of the at least one metabolite.

For example, the statistical analysis is a multivariate statistical analysis selected from the group consisting of principal component analysis, discriminant analysis, principal component analysis with discriminant analysis, partial least squares, partial least squares with discriminant analysis, canonical correlation, kernel principal component analysis, non-linear principal component analysis, factor analysis, multidimensional scaling, and cluster analysis.

For example, with respect to each one of the biological test sample profile and the predetermined profile, each one of the biological test sample profile and the predetermined profile is information configured to be provided in a respective region of a score plot using multivariate statistical analysis. As a further example, with respect to each one of the biological test sample profile and the predetermined profile, each one of the profiles is information configured to be provided on a respective region of a score plot using the multivariate statistical analysis.

In another embodiment, there is provided a method of providing a predetermined profile, wherein the predetermined profile is a disease state profile for a disease state caused or effected by pneumococcal infection.

In this respect, this includes providing a first data set. The providing of a first data set includes providing a plurality of disease state biological samples, wherein each one of the plurality of disease state biological samples includes a respective plurality of metabolites. A concentration of each one of the plurality of metabolites of a respective one of each one of the plurality of disease state biological samples is determined, such that a plurality of metabolite concentrations is provided for a respective one of each one of the plurality of disease state biological samples, wherein the plurality of metabolite concentrations of a respective one of each one of the plurality of disease state biological samples represents a disease state sample metabolite concentration set, such that there is provided a plurality of disease state sample metabolite concentrations sets, and wherein the first data set includes the plurality of disease state sample metabolite concentration sets.

For example, with respect to the plurality of disease state biological samples, each one of the plurality of disease state biological samples is a biological sample obtained from a human disposed in a disease state effected or caused by a pneumoccal infection.

For example, with respect to the plurality of disease state biological samples, each one of the plurality of disease state biological samples is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, or sputum. For example, each one of the plurality of disease state biological samples is urine.

For example, with respect to the concentration of each one of the plurality of metabolites of a respective one of each one of the plurality of diseased state biological samples, the concentration determination of each one of the plurality of metabolites of a respective one of each one of the plurality of diseased state biological samples includes using a spectrometric technique, such as NMR spectroscopy. As a further example, the concentration determination of each one of the plurality of metabolites of a respective one of each one of the plurality of diseased state biological samples includes using a spectrometric technique, such as NMR spectroscopy, to produce respective NMR spectroscopy information, and then converting the respective NMR spectroscopy information to the respective concentration.

This also includes providing a second data sat. The providing of a second data set includes providing a plurality of control biological samples, wherein each one of the plurality of control biological samples includes a respective plurality of metabolites. A concentration of each one of the plurality of metabolites of a respective one of each one of the plurality of control biological samples, such that a plurality of metabolite concentrations is provided for a respective one of each one of the plurality of control biological samples is determined, wherein the plurality of metabolite concentrations of a respective one of each one of the plurality of control biological samples represents a control sample metabolite concentration set, such that there is provided a plurality of control sample metabolite concentrations sets, and wherein the second data set includes the plurality of control sample metabolite concentration sets.

For example, with respect to the plurality of control biological samples, each one of the plurality of control biological samples is obtained from a human disposed in a state other than in a disease state effected or caused by pneumococcal infection. For example, the human disposed in a state other than in a disease state effected or caused by pneumococcal infection is not infected with a pneumococcal infection. As a further example, the human disposed in a state other than in a disease state effected or caused by the pneumococcal infection is healthy.

For example, with respect to the plurality control biological samples, each one of the plurality of control biological samples is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, or sputum. For example, each one of the control biological samples is urine.

For example, with respect to the concentration of each one of the plurality of metabolites of a respective one of each one of the plurality of control biological samples, the concentration determination of each one of the plurality of metabolites of a respective one of each one of the plurality of control biological samples includes using a spectrometric technique, such as NMR spectroscopy. As a further example, the concentration determination of each one of the plurality of metabolites of a respective one of each one of the plurality of control biological samples includes using a spectrometric technique, such as NMR spectroscopy, to produce respective NMR spectroscopy information, and then converting the respective NMR spectroscopy information to the respective concentration.

A log transformation of each one of the plurality of metabolite concentrations of a respective one of each one of the plurality of diseased state sample metabolite concentration sets of the first data set is effected to provide a corrected plurality of diseased state sample metabolite concentration seta, such that a corrected first data set includes the corrected plurality of diseased state sample metabolite concentration sets. A log transformation of each one of the plurality of metabolite concentrations of a respective one of each one of the plurality of control sample metabolite concentration sets of the second data set is also effected to provide a corrected plurality of control sample metabolite concentration sets, such that a corrected second data set includes the convicted plurality of control sample metabolite concentration sets.

A multivariate statistical analysis of the corrected first data set and the corrected second data set produces the disease state profile. For example, the multivariate statistical analysis produces an other than disease state profile. For example, with respect to each one of the disease state profile and the other than disease state profile, each one of the profiles is information configured to be provided in a respective region of a score plot using the multivariate statistical analysis. As a further example, with respect to each one of the disease state profile and the other than disease state profile, each one of the profiles is information configured to be provided on a respective region of a score plot using the multivariate statistical analysis.

The invention will be further described with reference to the following non-imitative examples.

EXAMPLE No. 1

I—Methods
Sample Collection and Preparation:

Normal subjects: A total of 59 volunteer subjects, self identified as normal, constituted the control group. Urine samples were collected twice daily - once as the first void sample in the morning and the second around 1700 h.

Patients in a disease state caused by *S. pneumoniae* infections (also sometimes referred to hereinafter as "pneumococcal patients"). A total of 59 patients infected with *S. pneumoniae*, as determined through cultures of blood, sputum, cerebrospinal fluid, bronchoalveolar lavage samples, endotracheal tube secretions, ascites or a combination of any of these, constituted the pneumococcal infection group.

Written informed consent was obtained from each patient and normal subject before entering this study, and the study protocol was approved by the institutional ethics committee.

Sample processing: Upon acquisition of urine samples, sodium azide was added to a final concentration of approximately 0.02% to prevent bacterial growth. Urine was placed in the freezer and stored at −80° C. until ready for preparation and data acquisition.

Sample preparation: Urine samples from healthy individuals were prepared by adding 70 µL of internal standard (Chenomx Inc.) (consisting of ~5 mM 2,2-dimethyl-2-silapentane-5-sulfonate (DSS), 100 mM Imidazole, 0.2% sodium azide in 100% D2O) to 630 µL of urine. Urine samples from the pneumococcal patients were prepared by adding 80 µL of the Chenomx internal standard to 820 µL of urine. Sample pH was adjusted to approximately 6.8 by the addition of small amounts of NaOH or HCl. 600 µL of sample was placed in a 5 mm NMR tube and stored at 4° C. until ready for data acquisition.

NMR Data Acquisition and Processing:

NMR spectra were acquired using the first increment of the standard NOESY pulse sequence on a 4-channel Varian Inova 600 NMR spectrometer with triax-gradient 5 mm HCN probe. All spectra were recorded at 25° C. with a 12 ppm sweepwidth, 1 s recycle delay, 100 ms $\tau_{mix}$, an acquisition time of 4 s, 4 dummy scans and 32 transients. $^1$H decoupling of the water resonance was applied for 0.9 s of the recycle delay and during the 100 ms $\tau_{mix}$. All spectra were zero-filled to 128 k data points and multiplied by an exponential weighting function corresponding to a line-broadening of 0.5 Hz.

Concentration Determination:

Quantification of urinary components was achieved using the 600 MHz library from Chenomx NMRSuite 4.0 (Chemomx Inc., Edmonton, Canada), which uses the concentration of the added DSS to determine the concentration of metabolites. The Chenomx 600 database was validated against a set of known compound concentration, using the same NMR data collection parameters as used in this study and donned accurate to better than 15% for all compounds reported (ie. error rate is less than 15%).

Statistical Analysis:

Partial Least Squares—Discriminant Analysis (PLS-DA) was performed using standard procedures as implemented in Simca P 11.0 (Umertics AB, Umed, Sweden). Input variables consisted of raw compound concentrations. Data were pre-processed by mean-centering and Pareto scaling prior to analysis.

ANOVA was done using the program StatView 5.0.1 (SAS Institute Inc., Cary, N.C., USA). Each metabolite was graphed as a histogram to test for normal distribution. For those metabolites that were not normally distributed, the results were subjected to a log transformation and re-plotted to check for normal distribution before ANOVA.

Correlation maps were created by calculating correlation matrices between each of the measured metabolite concentrations. The correlation of each element was calculated using $$r_{ik} = \frac{s_{ik}}{\sqrt{s_{ii}} \cdot \sqrt{s_{kk}}} \quad (1)$$

where $s_{ik}$ is the sample covariance between i and k, and was calculated as follows:

$$s_{ik} = \frac{1}{n} \sum_{j=1}^{n} (x_{ji} - \bar{x}_i)(x_{jk} - \bar{x}_k) \quad (2)$$

An appropriate color gradient was mapped onto the correlation values. A threshold was chosen to highlight important positive and negative correlation.

Heat maps were calculated as the deviation of each metabolite of the pneumococcal dataset from the mean of that metabolite of the control. The data were calculated as follows:

$$\frac{X_{PP} - \bar{X}_{Control}}{\sigma_{Control}} \quad (3)$$

II—RESULTS

A total of 59 patients in a disease state caused by pneumococcal infection, hereafter referred to in this example as the pneumococcal group, ranged in age from 6 days to 92 years (Table 1). In addition to the positive cultures indicated in Table 1, *S. pneumoniae* was also isolated from the cerebrospinal fluid of 3 patients, and from incites in 2 patients. The control group consisted of 29 males and 30 females ranging in age from 21 to 75 with a mean age of 43±±14 years.

TABLE 1

Selected features of the 59 patients in a disease state caused by S. pneumoniae infection

| | Total Number (% of Total) | Survivors (%) | Non-Survivors (%) |
|---|---|---|---|
| Number of Patients | 59 (100%) | 48 (81%) | 11 (19%) |
| Age (mean years ± SD) | 56 ± 22 | 55 ± 22 | 59 ± 25 |
| Male Gender (no, %) | 35 (59%) | 25 (52%) | 10 (91%) |
| Diabetes as underlying chronic illness | 9 (15%) | 5 (10%) | 4 (36%) |
| Bacteremia | 38 (64%) | 29 (60%) | 9 (82%) |
| Pneumonia | 36 (61%) | 28 (58%) | 8 (73%) |
| Bacteremic pneumococcal pneumonia | 23 (39%) | 17 (35%) | 6 (55%) |
| Probable pneumococcal pneumonia* | 5 (8%) | 4 (8%) | 1 (9%) |
| Possible pneumococcal pneumonia** | 16 (27%) | 15 (31%) | 1 (9%) |

*Probable pneumococcal pneumonia is defined as a positive culture in endotracheal tube secretions or bronchoalveolar lavage samples but not blood samples.
**Possible pneumococcal pneumonia is defined as *S. Pneumoniae* isolated from respiratory culture, but does not meet criteria for pneumococcal pneumonia.

FIG. 1 depicts a comparison of typical $^1$H NMR spectra of sample urines from the control soup (C,D) with approximate age and gender matched individuals from the pneumococcal group (A,B). Spectra were scaled according to the intensity of the creatinine resonances at approximately 3 and 4 ppm. While there are some differences between the spectra of the two controls, there are major differences between the spectra of controls versus the pneumococcal group. Citrate, which is a strong signal in the control spectra, is very low in the pneumococcal spectra. Carnitine and acetylcarnitine have much stronger signals in the pneumococcal spectra versus the control spectra. In addition, the 58 year-old pneumococcal female patient had very high levels of creatine, but the levels of creatine in the 26 year old pneumococcal male patient were quite low. Other major differences between the control and pneumococcal spectra may be observed in the 6-8 ppm range. Some of the measured major metabolite differences are shown in Table 2.

Many metabolites exhibited large deviations in their measured concentrations. For example, several of the pneumococcal patients had diabetes, and thus had extremely high levels of glucose in their blood. Histograms (not shown) indicated that almost every metabolite exhibited non-normal distribution either in the control set or the pneumococcal set. This type of behavior is not unexpected and is inherent in these types of data where a hard constraint of zero concentration is found at one end of the distribution. Upon log-transformation, the histograms revealed a normal distribution for all metabolites. Thus, for all data analysis presented herein, metabolite concentrations were log-transformed.

Univariate ANOVA was performed to test for significant differences in the means of each metabolite concentration between the control and pneumococcal group as well as the control and a subset of the pneumococcal group containing no diabetic patients (Table 2). ANOVA revealed 37 out of the 82 measured metabolites had significantly different means, and removal of the diabetic patients had little or no effect on the results of the ANOVA.

TABLE 2

Metabolite concentrations (μM)* measured from $^1$H NMR spectra in healthy subjects and *Streptococcus pneumonaie* infected patients.

| Metabolite | Healthy | S. pneumoniae |
|---|---|---|
| Quinolinate | 27 ± 2 | 72 ± 13 |
| 1-Methylnicotinamide | 21 ± 3 | 12 ± 3 |
| Trigonelline | 273 ± 48 | 73 ± 21 |
| Tryptophan | 55 ± 4 | 96 ± 12 |
| Citrate | 2443 ± 206 | 1289 ± 258 |
| Succinate | 114 ± 11 | 95 ± 15 |
| 2-Oxoglutarate | 64 ± 9 | 115 ± 15 |
| cis-Aconitate | 282 ± 22 | 360 ± 48 |
| trans-Aconitate | 59 ± 10 | 52 ± 6 |
| Fumarate | 4.5 ± 0.4 | 26 ± 4 |
| Guanidoacetate or UNKNOWN #1 | 181 ± 17 | 81 ± 11 |
| Creatine | 542 ± 97 | 1457 ± 307 |
| Creatinine | 11171 ± 752 | 10676 ± 1030 |
| Glycine | 1049 ± 110 | 765 ± 107 |
| Dimethylamine | 335 ± 22 | 486 ± 42 |
| TMAO | 305 ± 30 | 463 ± 98 |
| 3-Hydroxybutyrate | 18 ± 2 | 684 ± 534 |
| Acetone | 14 ± 3 | 150 ± 46 |
| Carnitine | 61 ± 7 | 516 ± 558 |
| Acetylcarnitine | 21 ± 2 | 199 ± 39 |
| Myo-inositol | 86 ± 8 | 924 ± 240 |
| 3-Aminoisobutyrate | 102 ± 18 | 193 ± 48 |
| Fucose | 58 ± 5 | 119 ± 14 |
| Glycolate or UNKNOWN #2 | 334 ± 25 | 259 ± 64 |
| Uracil | 34 ± 3 | 22 ± 3 |
| Pyroglutamate | 245 ± 18 | 343 ± 41 |
| Isoleucine | 9.5 ± 0.5 | 28 ± 5 |
| Valine | 25 ± 2 | 68 ± 10 |
| π-Methylhistidine | 652 ± 91 | 117 ± 21 |
| Acetate | 167 ± 31 | 478 ± 158 |
| Lactate | 146 ± 36 | 957 ± 309 |
| 1,6-Anhydro-β-D-glucose | 142 ± 25 | 55 ± 17 |
| 2-Aminobutyrate or UNKNOWN #3 | 13 ± 1 | 86 ± 14 |
| 2-Hydroxyisobutyrate | 47 ± 7 | 44 ± 6 |
| 3-Hydroxyisovalerate | 53 ± 4 | 49 ± 7 |
| 3-Indoxylsulfate | 178 ± 17 | 214 ± 35 |
| 4-Hydroxyphenylacetate | 93 ± 6 | 154 ± 30 |
| 4-Hydroxyphenyllactate | 11 ± 1 | 184 ± 132 |
| Adipate | 13 ± 1 | 90 ± 48 |
| Alanine | 225 ± 17 | 460 ± 383 |
| Allantoin | 82 ± 13 | 93 ± 28 |
| Arginine | 188 ± 12 | 283 ± 33 |
| Asparagine | 124 ± 11 | 198 ± 26 |
| Betaine | 50 ± 8 | 107 ± 15 |
| Ethanolamine | 272 ± 18 | 283 ± 55 |
| Formate | 301 ± 22 | 325 ± 86 |

TABLE 2-continued

Metabolite concentrations (μM)* measured from $^1$H NMR spectra in healthy subjects and *Streptococcus pneumonaie* infected patients.

| Metabolite | Healthy | S. pneumoniae |
|---|---|---|
| Glucose | 220 ± 18 | 12562 ± 7648 |
| Glutamine | 375 ± 25 | 331 ± 38 |
| Hippurate | 1842 ± 228 | 1959 ± 489 |
| Histidine | 604 ± 52 | 405 ± 67 |
| Hypoxanthine | 37 ± 4 | 83 ± 12 |
| Isopropanol or UNKNOWN | 22 ± 5 | 7 ± 1 |
| Leucine | 26 ± 2 | 91 ± 19 |
| Lysine | 124 ± 15 | 141 ± 16 |
| Mannitol | 358 ± 62 | 264 ± 52 |
| N,N-Dimethylglycine | 29 ± 3 | 28 ± 4 |
| Pyruvate or UNKNOWN | 21 ± 2 | 112 ± 22 |
| Serine | 250 ± 21 | 376 ± 51 |
| Tartrate or UNKNOWN | 73 ± 21 | 39 ± 11 |
| Taurine | 422 ± 80 | 1769 ± 343 |
| Threonine | 128 ± 10 | 180 ± 22 |
| Tyrosine | 76 ± 6 | 129 ± 15 |
| Urea | 234,000 ± 10,000 | 246,000 ± 24,000 |
| Xylose | 80 ± 8 | 116 ± 10 |
| τ-Methylhistidine | 177 ± 12 | 173 ± 23 |

*Measured concentrations are reported as average ± SEM. Concentrations have not been corrected for dilution.

FIG. 2 is a heat map showing each pneumococcal patient with the corresponding measured metabolite concentrations. For each patient, metabolites that are three (3) standard deviations or more different from the control group are indicated by the colors/shading shown. This figure illustrates the relationships between metabolite variables across the patient population in a similar manner as gene microarrays show the expression levels of genes. FIG. 2 shows that in the pneumococcal group, high levels of acetylcarnitine, carnitine, acetone, acetoacetate and 3-hydroxybutyrate were found whereas low levels of citrate, 1-methylnicotinamide and trigonelline were found. Interestingly, the patients with diabetes and pneumococcal disease did not appear much different from the patients with only pneumococcal disease.

FIG. 3.1A shows a scores plot from a PLS-DA analysis of pneumococcal group (circles) versus the healthy control group (squares). A clear separation between the groups is observed. To be sure that the separation was not affected by potential co-morbidities, such as diabetes, diabetic patients were removed from the PLS analysis (FIG. 3.1B). M was observed with the univariate analysis, the multivariate analysis was affected very little by excluding patients with diabetes. Furthermore, inspection of the individual data points within the PLS-DA plots illustrates no further discrimination of the patient population based on age, gender, or death (data not shown). In addition, clear separations of patients based on the type of pneumococcal infection was not observed in this case (data not shown).

FIGS. 3.1C and 3.1D are loadings plots for the PLS-DA shown in FIG. 3.1A and 3.1B respectively. Based on this analysis, the significant metabolties identified for separating the pneumococcal group from the control group are: citrate, trigonelline, 1-methylnicotinamide, acetylcarnitine, carnitine, acetate, and acetone. Acetoacetate may or may not be a significant marker. Interestingly, these were shown to be significant in the univariate ANOVA as well as heatmap data.

Figure 4:
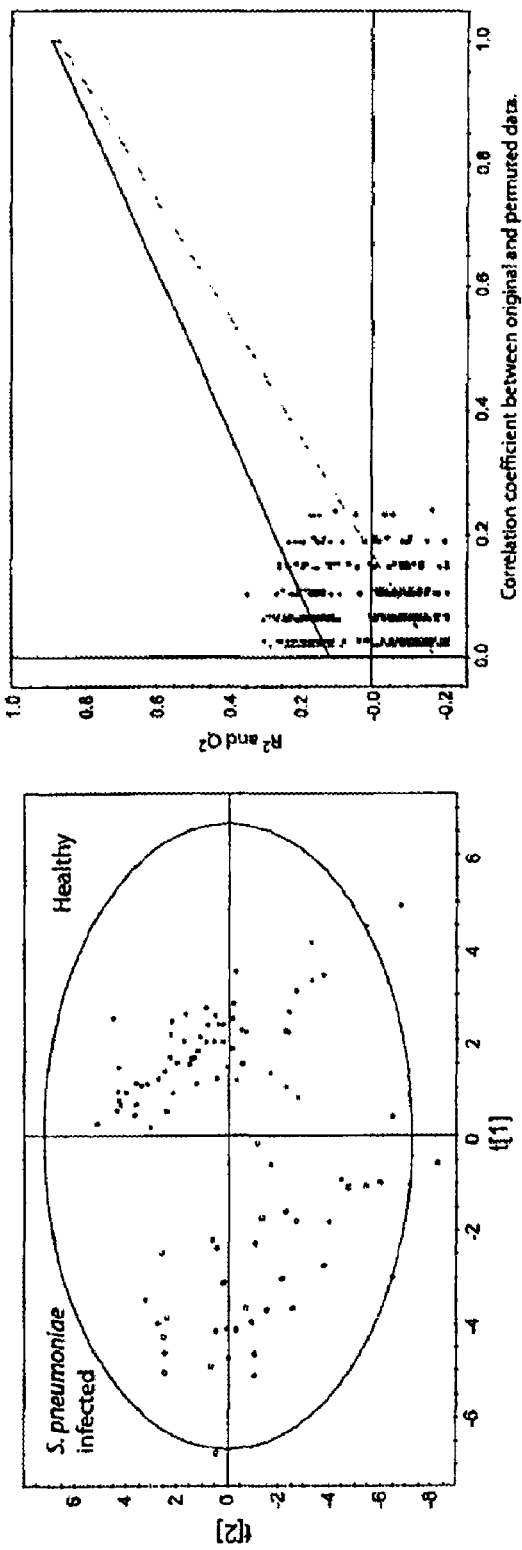
FIG. 4 shows a PLS-DA scores plot of urine derived from patients with *Streptococcus pneumoniae* infections compared to a "healthy" (non-TB) cohort. R2=0.89, Q2=0.87.

FIG. 4 shows a PLS-DA scores plot of urine derived from patients with *Streptococcus pneumoniae* infections compared to a "healthy" (non-TB) cohort. R2=0.89, Q2=0.87. Validation of the model confirms robustness. Data was prepared by applying a log-transform to the metabolite concentrations determined using Chenomx NMRSuite v4.0 software. Only patients who tested positive for Streptococcus pneumoniae and no other pathogen were included as part of the S. pneumoniae test set. Exclusions were not made for patients with co-morbidities such as diabetes. In total, 66 metabolites were quantified (see Table 2). The first 32 metabolites listed in Table 2 were used in the analysis. N=18 for patients infected with Streptococcus pneumoniae, and n=60 healthy subjects. Sensitivity=89%, specificity=100% for the test. One healthy subject and four Streptococcus pneumoniae patients were classified as neither class and were deemed outliers.

EXAMPLE 1.1

After Example 1.0, a second quantification of urinary components using the same NMR data of Example 1.0 was achieved using the 600 MHz library from Chenomx NMR-Suite 4.6 (Chenomx Inc., Edmonton, Canada), which uses the concentration of the added DSS to determine the concentration of metabolites. The Chenomx 600 database was validated against a set of known compound concentrations using the same NMR data collection parameters as used in this study and deemed accurate to better than 15% for all compounds reported. Statistical analysis was then applied in the manner outlined for Example 1.0.

FIG. 3.2A shows a scores plot from a PLS-DA analysis of pneumococcal group (circles) versus the healthy control grew (black square). A clear separation between the maps is observed. As was observed with the univariate analysis, the multivariate analysis was affected very little by excluding patients with diabetes. Furthermore, inspection of the individual data points within the PLS-DA plots illustrates no further discrimination of the patient population based on age, gender, or death (data not shown). In addition, clear separations of patients based on the type of pneumococcal infection was not observed in this case (data not shown).

FIG. 3.2B is a loadings plots for the PLS-DA shown in FIG. 3.2A. Based on variable importance in the projection (VIP) analysis, the significant metabolties identified for separating the pneumococcal group from the control group are: citrate, trigonelline, acetylcarnitine, acetone, myo-inositol, 3-hydroxybutyrate, glucose and carnitine. Interestingly, these were shown to be significant in the univariate ANOVA.

III—Discussion

Using both univariate and multivariate analysis techniques on metabolite concentrations determined for 67 compounds using 1H NMR spectroscopy, it was determined that several compounds were responsible for separating the pneumococcal group from the healthy controls (Table 2). The elevated levels of glucose and ketone bodies (acetone, acetoacetate, and 3-hydroxybutyrate) in some patients may due to the fact that some are diabetic (9 patients in total), but may also be indicative of alterations in energy substrate-endocrine relationships. Indeed, it has been found that the NMR spectra of urine from intra-operative patients showed increases in urinary excretion of alanine, ketone bodies, lactate and glucose over time that correlated specifically to the degree of surgical stress. Presumably, the ketone bodies indicate a shift to the use of fatty acids for energy product. As well, a rise in ketone body concentration coupled with a rise in acetylcarnitine concentration has also been shown in fasting healthy subjects. Interestingly, increased levels of taurine were observed; increase taurine levels have been previously shown to be associated with liver damage. In a separate study, bacteremic pneumococcal patients were found to have high bililrubin concentrations. Some patients had high levels of trimethylamine-N-oxide (TMAO), dimethylamine, acetate, and lactate and low levels of citrate which has previously been shown to be related to kidney dysfunction.

In 80% of patients with pneumococcal disease, acetylcarnitine was elevated by two (2) standard deviations or more and 66% of patients had substantially elevated levels of carnitine (Table 2). Both compounds were elevated beyond ten (10) standard deviations for a number of patients (FIG. 2). Synthesis of acetylcholine has been shown to be stimulated by glucose, carnitine or acetylcamitine. Carnitine has also been shown to be an essential cofactor for the transport of fatty acyl groups into the mitochondrial matrix. In addition, carnitine has bean found to be metabolized into trimethylamine which is absorbed, converted to trimethylamine-N-oxide in the liver and excreted in the urine. This may explain higher levels of trimethylamine and TMAO in some patients. Of interest, acetylcarnitine has also been shown to be used in the brain for the production of releasable glutamate rather than as an energy source.

Univariate ANOVA suggests that any one of the 37 significant compounds should be a useful biomarker for pneumococcal disease. However, the best biomarker (elevated in the most patients by 2 standard deviations) would only predict pneumococcal disease WA of the time. This is in the order of current testing technologies and it is not known at this time whether this biomarker would be specific for pneumococcal infection or for a number of bacterial infections. Thus, multivariate analysis techniques, and in particular PLS-DA, was used for analysis. Out of 59 pneumococcal patients, one overlapped with the control set (FIG. 3.1A). This datapoint came from a patient admitted to the ER because of a drug overdose who tested positive for S. pneumoniae in a sputum sample, but did not test positive in a blood culture. Since there was no evidence of pneumonia on chest way, this patient was likely colonized with S. pneumoniae, suggesting that carriers and infected individuals may, potentially, be differentiated.

A survey of the pneumococcal patients who died (7 non-diabetics) revealed higher levels of lactate, leucine, and myo-inositol, and lower levels of 1-methylnicotinamide, citrate, acetylcarnitine, carnitine and taurine when compared to the survivors.

EXAMPLE No. 2

I Methods
Populations:

Written informed consent was obtained from each subject and patient before entering this study, and the institutional ethics committees approved the protocols outlined below.

Patients in a disease state caused by pneumococcal disease (all pneumonia): Pneumonia was categorized as definite pneumococcal pneumonia: positive blood culture for S. pneumoniae (n=37); or possible pneumococcal pneumonia; positive sputum or endotracheal tube culture for S. pneumoniae only (n=15). All patients had a chest X-ray radiograph read as pneumonia by a radiologist. In addition, 2 of the blood positive patients had pneumococcal peritonitis (S. pneumoniae isolated from pleural fluid) and 2 of the blood-positive patients had meningitis (S. pneumoniae isolated from cerebrospinal fluid). S. pneumoniae was identified in microbiology laboratories of the University of Alberta Hospital and Mt Sinai Hospital using standard criteria. For the entire group: n=52 (31 male, 21 female); mean age: 53±23; range: 6 days-88 years. In addition, this group had 8 diabetics.

Healthy volunteers: n=115, (45 male, 70 female); mean age: 59±14; range: 19-87. This group had 3 diabetics.

Non-Infectious metabolic stress: Patients in this category were diagnosed with (1) myocardial infarction: n=12; (10 male, 2 female); mean age: 59±14, range: 41-76, (2) congestive heart failure: n=12; (7 male, 5 female); mean age: 78±9, range: 59-91, (3) trauma (fractures): n=17; (11 male, 6 female); mean age: 55±14, range: 22-76, (4) trauma (lacerations): n=14; (10 male, 4 female); mean age: 32±13, range: 19-57, and (5) other: n=1 (1 female); age=37. In all instances, the patient's attending physician made diagnoses of the above conditions. Patients in groups (1)-(3) had no obvious evidence of infection.

Longitudinal study: Serial urine study: Patients presenting with pneumonia caused by *S. pneumoniae*, (n=12) had samples collected upon admission to hospital, and 10 days post-admission after treatment with antibiotics.

Comparison to other lung infections: Patients with Legionnaires' disease: n=74; (22 male, 52 female); mean age: 66±19, range: 22-94. Patients with *Mycobacterium tuberculosis* infection: n=30; (20 male, 10 female); mean age: 56±19, range: 22-96.

Blinded study: A set of urine samples was assembled from patients not part of the original learning set with the following: bacteremic pneumococcal pneumonia n=35; healthy n=42; non-infectious stress n=9; COPD=6; Asthma n=8; Tuberculosis n=24; Legionnaires' disease n=1; Q-fever n=20. The etiological diagnoses were unknown to the investigator who analyzed the samples and provided a diagnosis from metabolite concentrations before the code was broken.

Cell Culture and Mouse Models.

Bacteria. *S. pneumoniae* serotype 14 (strain 04SR2228), grown on blood agar plates, was cultured on Todd-Hewitt (THB) broth for 7 hours until mid-log phase of exponential growth. The bacterial suspension was washed three times by centrifugation and re-suspended in pre-warmed THB prior to all experiments.

Mice. C57Bl/6 mice were purchased from Charles River Laboratory, Canada and were between 8 and 10 weeks of age at the time of experiment. Blood (serum), urine, and BAL samples were collected as described in Supplementary Methods.

Cell Culture. Human bronchial epithelial A549 all culture studies were performed as described in Supplementary Methods attached as Appendix I.

Data collection. Urine samples obtained from human volunteers were treated as described[19]. Urine samples obtained from mice and cell culture supernatants were filtered through 3 kDa MW cutoff filters, and diluted with $H_2O$ to 585 µL. Internal standard containing DSS-d6, $NaN_3$ and $D_2O$ (65 µL), and pH was adjusted to ~6.8.

NMR spectra were acquired as previously described[19]. Analysis of these data was accomplished using targeted profiling through the use of Chenomx NMR Suite 4.6 (Chenomx Inc. Edmonton, Canada) and concentrations determined as previously described[19].

Data analysis. Multivariate data analysis was performed on $log_{10}$-transformed metabolite concentrations using SIMCA-P (version 11, Umetrics, Umed, Sweden) that had been mean centered and unit variance scaling applied. The number of components for both PCA and PLS-DA models were chosen using a 7-fold cross validation rule. Box and whisker plots as well as significance tests using two-tailed Mann-Whitney non-parametric analysis was performed using GraphPad Prism version 4.0c for Macintosh (GraphPad Software, San Diego, USA).

Receiver operating curves were generated using SPSS software (SPSS Inc, Chicago, USA).

II Results

Metabolic Profile of Urine of Subjects in a Disease State Caused by *S. pneumoniae* Infection Comparison of 62 metabolite concentrations measured in urine from age and gander matched infected (with *S. pneumoniae*) and non-infected subjects revealed complete class distinction using PCA (principal components analysis) (FIG. 5a). No distinction was observed between those with bacteremia and those with positive sputum or endotracheal tube culture (FIG. 5a). Removal of the eight diabetics from the pneumococcal group, and three from the "healthy" group did not affect the distribution (FIG. 5b). PLS-DA (partial least squares-discriminant analysis) applied to the entire dataset, to both optimize visualization and supervise the model using class labels, showed clear distinction between pneumococcal patients and "healthy" subjects (FIG. 5c). This group included pneumococcal patients as young as 6 days, and a larger number of "healthy subjects". A total of two components were calculated, and validation revealed an excelled predictive model with $R^2$ of 0.87 and a $Q^2$ of 0.85.

Out of a total of 62 quantified metabolites, 13 decreased in concentration, 24 increased, and 21 remained unchanged when comparing subjects infected with *S. pneumoniae* to uninfected subjects. Of the 13 metabolites that decreased significantly ($p<0.05$), several are involved with energy metabolism including citrate, succinate (tricarboxylic acid cycle (TCA) intermediates), and 1-methylnicotinamide (nicotinamide metabolism). Other metabolites that drop in concentration are associated with food intake (levoglucosan, and trigonelline), and gut microflora (hippurate). Glycine, ethanolamine, uracil, dimethylglycine, guanidoacetate, glycolate, and π-methylhistidine were also observed to decrease. Metabolites that increased in concentration included amino acids (alanine, asparagine, isoleucine, leucine, lysine, swine, threonine, tryptophan, tyrosine, and valine), those involved with glycolysis (glucose, acetate, lactate), fatty acid oxidation (3-hydroxybutyrate, acetone, carnitine, acetylcarnitine), inflammation (hypoxanthine, fucose), osmolytes (myo-inositol, taurine), and creatine. Of interest, the TCA cycle intermediates 2-oxoglutarate and fumarate appeared to increase in human urine upon pneumococcal infection. Metabolites that did not change with infection included creatinine, some amino acids (glutamine, histidine and pyroglutamate), τ-methylhistidine, aconitate (tram and cis), metabolites related to gut microflora (3-indoxylsulfate, 4-hydroxyphenylacetate, allantoin, and TMAO (trimethylamine-N-oxide)), dietary metabolites (mannitol, propylene glycol, sucrose, tartrate), and others.

Since most patients with pneumococcal pneumonia would experience metabolic stress from infection, it was investigated whether some of the observed response might be due to stress. A group of patients with non-infectious metabolic stress, defined as anyone presenting to the emergency room with a condition other than an infectious disease, consisted of fractures (31%), myocardial infarcts (24%), lacerations (24%), congestive heart failure (21%), and others (1%). Comparison between the normal, healthy group and the stress group revealed class distinction (FIG. 5d). A total of 2 components separated the groups, ($R^2=0.62$, and $Q^2=0.56$) with most separation in component 1. Validation of the PLS-DA model revealed a robust model. However, comparison of the stressed group with the pneumococcal and normal groups together revealed that the stressed group was distinct from both (FIG. 5e). A total of four components separated the three groups with an $R^2$ of 0.71, and a $Q^2$ of 0.58. While the difference between the pneumococcal and normal groups was observed primarily in components 1 and 2, the difference between the stressed group and both the pneumococcal and normal groups was seen in component 3.

Compression of Metabolic Profile of Wine of Human Subjects Infected with *S. pneumoniae* and Mouse Subjects Infected with *S. pneumoniae*.

Figure 6A:
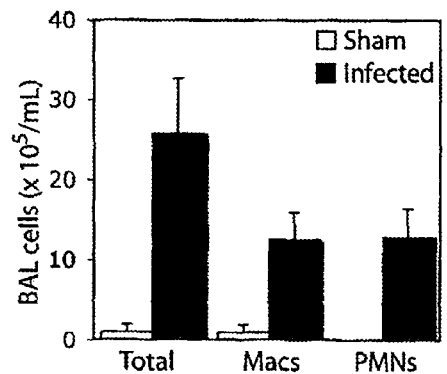
FIG. 6: a, Inflammatory infiltrates in BAL of mice infected with *S. pneumoniae* serotype 14 versus sham. b, Lung histology of mice infected with *S. pneumoniae* serotype 14 compared with sham treatment. The sections are representative of at least three different mice. Bar represents 100 μm at 20×, 50 μm at 40×. c, PCA model of urinary metabolite concentrations determined 24 h post-treatment of mice with either *S. pneumoniae* (○, n=14) or sham (■, n=12). d, Box and whisker plots of urine and serum metabolite concentration differences between sham mice (n=12) and mice infected with *S. pneumoniae* (n=14); *: $p<0.05$; : $p<0.01$; *: $p<0.001$. Only urine concentration of creatinine is shown as the concentration of creatinine in serum was below the detection limit.
Figure 6B:
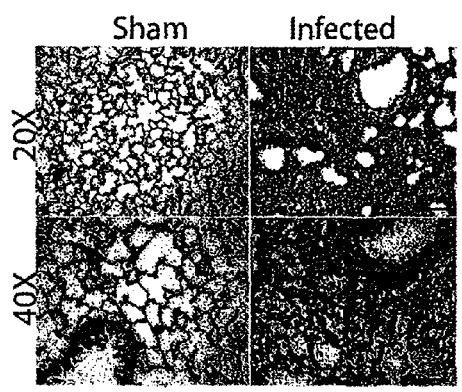
Figure 6C:
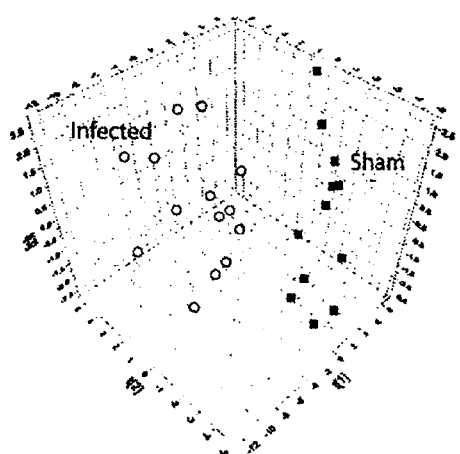

Since not all factors (such as co-morbidities and drug usage) could be controlled in the human population, a mouse model of pneumococcal pneumonia was used to see if metabolic changes specific to pneumococcal infection could be observed. Intra-tracheal injection of C57Bl6 mice with either bacterial growth media (sham) or growth media containing $10^7$ cfu of *S. pneumoniae*, serotype 14 (inflected) revealed an increase in macrophages end neutrophils in the HAL fluid after 24 h (FIG. 6a). Histologically, the features of bacterial pneumonia were evident with alveolar spaces filled with an inflammatory exudate consisting of polymorphonuclear leukocytes and macrophages (FIG. 6b). PGA was carried out on 46 measured metabolite concentrations in the urine of the sham and infected animals revealing strong separation (FIG. 6c) with an $R^2$ of 0.83, and a $Q^2$ of 0.74. Out of 46 metabolites measured in the mouse urine, 18 decreased in concentration, 5 increased (significance $p<0.05$), and 23 remained unchanged upon infection with *S. pneumoniae*. The TCA cycle intermediates (citrate, succinate, 2-oxoglutarate, fumarate, and aconitate) were among those that decreased in concentration, as well as trigonelline, glycolate, and glycine. Creatine, fucose, and taurine increased in concentration while creatinine concentration, or those metabolites associated with gut microflora (3-indoxylsulfate, allantoin, and TMAO) were unaltered. Since many of the metabolites measured in human urine were not measurable in mouse urine, and some metabolites found in mouse urine were not measurable in human urine, direct comparison of all metabolites could not be accomplished. However, of the metabolites that could be directly compared between human and mouse mine (35), 13 performed similarly (glycine, creatinine, creatine, citrate, succinate, fucose, 3-indoxylsulfate, allantoin, hippurate, TMAO, trigonelline, glycolate, and taurine).

Figure 6D:
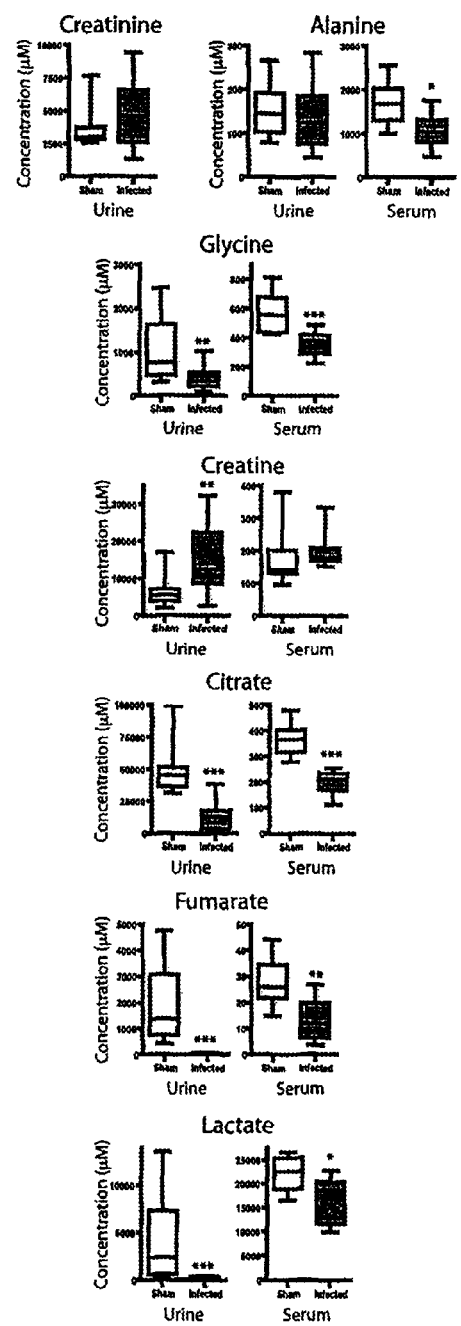

To investigate whether similar metabolic changes could be observed in urine and blood, a comparison of urinary and serum metabolites was made between sham and infected mice (FIG. 6d). While urinary creatinine was not statistically different between the groups, metabolites that were observed to decrease in urine (glycine, citrate, fumarate, and lactate) also decreased in serum. Of interest, while alanine had similar concentrations in the urine of the sham and infected animals, it decreased in serum upon infection. Other metabolites that were observed to increase in urine (creatine) also tended to increase in serum.

Metabolic Changes in Cell Cultures.

Figure 7:
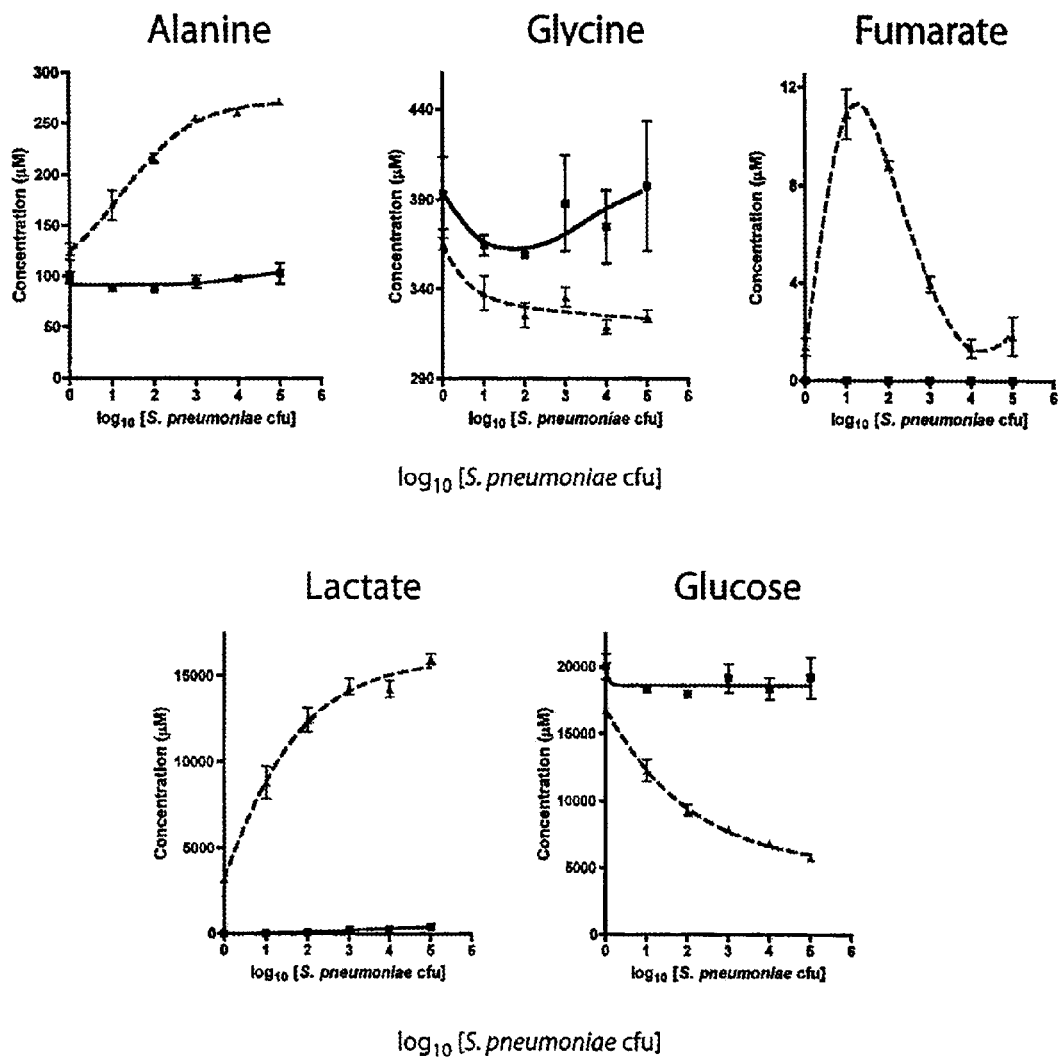
FIG. 7: Metabolite analysis of cell culture supernatants of A549 cells after 24 hours of incubation with specified cfu/100 μL *S. pneumoniae*. Bacteria in DMEM media alone (■); Bacteria in culture with A549 cells in DMEM (▲). The first point (on the y-axis) represents supernatant metabolite concentrations of A549 incubated in DMEM for 24 h. Each point represents the average of three separate experiments.

To determine whether some metabolic changes observed in the urinary profiles could be due to direct infection of lung epithelial cells by *S. pneumoniae*, cell cultures of human bronchial epithelial A549 cells ($10^6$ cells/well) were incubated with increasing concentrations of *S. pneumoniae* (serotype 14) bacteria (0, $10^1$, $10^2$, $10^3$, $10^4$, $10^5$ cfu/mL) for 24 h. Control plates were also cultured containing bacteria alone. Comparison of supernatant metabolites between control cultured bacteria and bacteria incubated with A549 cells revealed both increases and decreases of several amino acids in the supernatant (FIG. 7). The amino acids alanine (FIG. 7), arginine, aspartate, glutamate, histidine, proline, serine, and threonine (not shown) all increased in concentration in correlation with bacterial load, as did the TCA-cycle intermediate succinate. While some amino acids decreased in concentration (asparagine, glycine (FIG. 7), glutamine), several did not change (isoleucine, leucine, lysine, methionine, phenylalanine, tryptophan, tyrosine and valine). Fumarate was observed to initially increase then decrease at higher doses of *S. pneumoniae* (FIG. 7). Interestingly, while acetate and lactate (FIG. 7) increased dramatically, glucose (FIG. 7) and pyruvate decreased in cell culture supernatants. Also, of interest, acetone and formate, both indicators of fatty acid oxidation in the peroxisome, increased dramatically, whereas 2-oxoisocaproate and 3-methyl-2-oxovalerate, both involved in leucine metabolism and synthesized in mitochondria, decreased markedly in concentration (not shown).

In total, out of 31 measured metabolites in cell culture supernatants, 7 were observed to decrease, 14 increased, 2 increased at low doses of bacteria then decreased at higher doses, and 8 were not altered. Comparison of the meowed metabolites in common between the cell culture and human urine (20 metabolites), revealed similarities for seven metabolites (alanine, glycine, swine, threonine, acetate, lactate, and acetone).

Metabolite Profiles Return to Baseline.

Figure 8A:
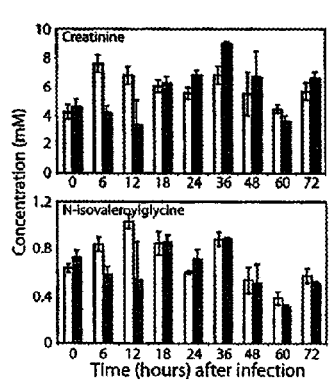
FIG. 8: Metabolite analysis of mouse and human urine. a-c, Column graphs indicating metabolite concentration differences between sham mice (□) and mice infected with *S. pneumoniae* (■). Error bars reflect the average concentration among 3 to 8 mice. Metabolites shown are those that a, remain similar for both groups b, increase in concentration with infection and c, decrease in concentration with infection. d, Box and whisker plot of urinary metabolite concentrations as patients recover from *S. pneumoniae* infection compared to healthy (non-infectious) subjects. The day 10 subjects (n=12) are a subset of the day 1 subjects (n=69). Significance is indicated pairwise compared to the "healthy" set; * indicates $p<0.001$;  indicates $p<0.01$; * indicates $p<0.05$.
Figure 8B:
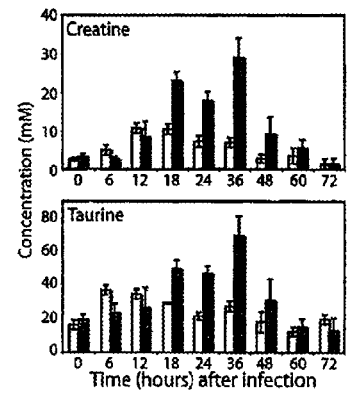
Figure 8C:
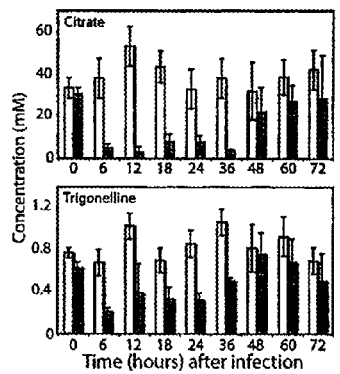

To investigate whether urinary profiles of infected mice returned to baseline values at later times, urine samples were collected from C57Bl/6 mice prior to infection and at regular intervals for three days. Some metabolites (creatinine and N-isovaleroylglycine) remained constant throughout the experiment (FIG. 8a). Other metabolites increased at ~18 hours post-infection (creatine and taurine), returning to their original values near 48 h (FIG. 8b). Finally other metabolites, such as citrate and trigonelline, showed significant decreases immediately (6-12 h) after infection, than returned to baseline 48 h post-infection (FIG. 8c). In general, all metabolites that altered significantly ($p<0.05$) with infection, had maximal changes at ~24 h concomitant with observation of health state (activity levels of the infected mice decreased steadily to 24 h, and then appeared to increase starting at ~36 h).

Figure 8D:
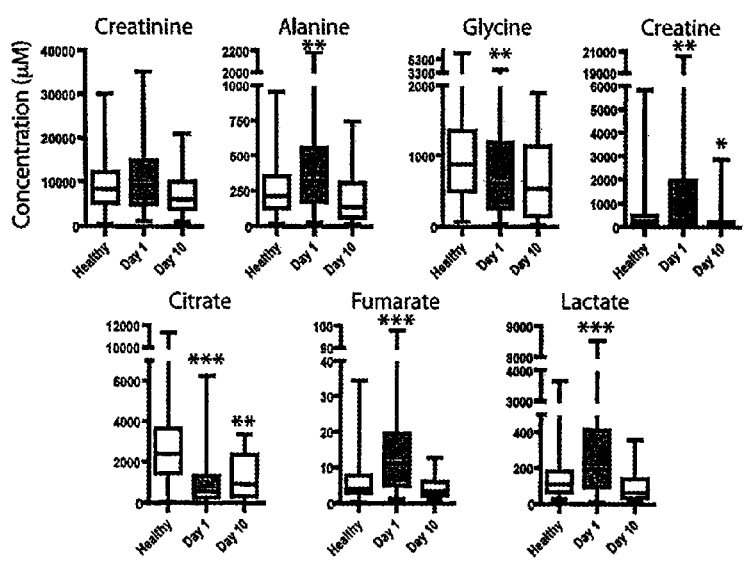

Comparison of normal subjects, pneumonia patients (day 1) and patients ten days after diagnosis revealed an overall shift in urinary metabolite concentrations to baseline levels 10 days post-therapy in patients (FIG. 8d). Analysis of metabolites revealed that creatinine concentrations were similar across all groups. Others, such as alanine, creatine, fumarate, and lactate, increased with infection, but either returned or started to return to baseline 10-days post therapy. In contrast, while glycine and citrate decreased with infection, by 10 days, citrate started to recover to baseline, as the difference between normal subjects and those 10 days post-infection was less than the difference between normal and those at the at of treatment.

Comparison of Profiles Between *S. pneumoniae* and Other Types of Pneumonia.

To investigate whether metabolic differences seen between pneumococcal pneumonia and "healthy" were specific for *S. pneumoniae* infection, a comparison was made to other types of pneumonia. Comparison of urinary metabolic signatures of normal subjects, pneumococcal pneumonia patients, and Legionnaires' patients revealed excellent class distinction (FIG. 9a), with discrimination between pneumococcal patients and healthy subjects occurring primarily in the first component, and between Legionnaires' and pneumococcal and healthy subjects in the third component. Validation of the model reveals a robust model with as $R^2$ of 0.76, and $Q^2$ of 0.69.

Comparison of pneumococcal pneumonia with *L. pneumophila* and *M. tuberculosis* also revealed an excellent model as well with an $R^2$ of 0.83 and a $Q^2$ of 0.69 (FIG. 9b).

Blinded Study.

Figure 10:
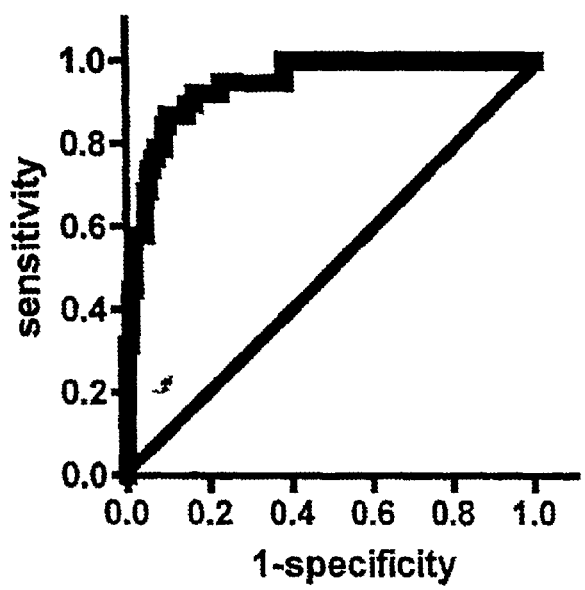
FIG. 10: Receiver operating characteristic curve (ROC) for diagnosis of *S. pneumoniae* pneumonia. The AUC for the blinded test set was 0.944.

To test the robustness of the model in correctly predicting *S. pneumoniae* infection with only measured urinary metabolite concentrations, an independent sample set composed of 145 samples was blindly and randomly selected. In this sample set, 35 were from bacteremic pneumococcal patients; 42 were normal subjects; 9 from patients with non-infectious metabolic stress; 14 from COPD*/asthma patients; anti 45 were other pneumonia etiologics including those with *M. tuberculosis, L. pneumophila*, and *C. burnetti*. An ROC curve (FIG. 10) with an AUC (area under curve) of 0.944 revealed that this test was both sensitive (86%) and specific (94%) for diagnosis of bacteremic pneumococcal pneumonia.

*"COPD" is Chronic Obstructive Pulmonary Disease

PLS-DA was used to evaluate differences in urinary metabolite levels between individuals with pulmonary *S. pneumoniae* infection and those considered normal. Compounds that were considered significantly different between those with pulmonary *S. pneumoniae* infection and normal were discovered by algorithms within the SIMCA P package and used to build "class predictors". The class predictors were then used on a "blinded" set of urine samples where the diagnosis was unknown at the time of class prediction. Using 145 urine samples from patients ranging in age from 2 to 90 years, 30/35 patients with a pulmonary *S. pneumoniae* infection were correctly predicted, and 7/110 were correctly predicted as not having a pulmonary *S. pneumoniae* infection.

FIG. 11 summarizes the characteristics of the false negatives and false positives. Examination of the metabolite profiles for each false negative patient revealed that many of the metabolites were similar to those infected with *S. pneumoniae*. The first patient was classified as non-pneumococcal pneumonia because of "normal" creatine and taurine values. Patients 2-4 had "normal" levels of carnitine and acetylcarnitine. Patient 5 had a very high level of citrate (11 mM), whereas most pneumococcal patients have a citrate concentration <1 mM.

False positives included 1 patient with chronic obstructive pulmonary disease (COPD), I patient with congestive heart failure, 1 patient with a laceration (all presenting to the emergency department), and four tuberculosis (TB) patients who were within 2 weeks of diagnosis. There was no indication of an *S. pneumoniae* infection for any of these patients.

III Discussion

A metabolomic diagnostic approach for a disease state effected or caused by an infectious lung disease using urine is herein illustrated. A definitive metabolic profile specific to a disease state caused by lung infection with *S. pneumoniae* was seen in a mouse model indicating the human profile likely arises from infection. Moreover, similarities in ~⅓ of common metabolites found in human urine with mouse urine and cell culture supernatant indicate that the metabolite profile observed is due to both the infection and immune response. Changes observed in mouse urine were similar to changes in serum validating the use of urine as a diagnostic medium. Longitudinal studies for both mouse and human subjects revealed that urinary metabolite profiles can return to "normal" values, and that the profile changes over the course of the infection. These results are particularly significant, since infection can start before significant symptoms, and infection can continue well beyond the infectious period.

In a completely blinded test set, only seven patients out of 110 "true negatives" presented with a false positive for an *S. pneumoniae* infection, and all may have had a concomitant *S. pneumoniae* infection even if they had a negative blood culture. Of the false negative patients (five out of 35 "true positives"), four out of five patients had chest X-rays that indicated a consolidation, and blood and urine creatinine levels did not indicate kidney dysfunction. Examination of metabolite profiles for these patients revealed that most metabolites were more similar to *S. pneumoniae* than normal. For one patient, citrate levels were extremely high (>11 mM), whereas for most individuals with *S. pneumoniae* infection, citrate is very low (<1 mM). In the other four cues, the patients were classified as "normal" because two metabolites that are normally high in infected individuals were in the lower end of the "normal" range. Two of these patients were immunocompromised (one HIV and one cancer patient), and thus may have presented earlier for medical attention. Indeed, not all metabolites changed at the same point in time in mice, and potentially these patients could be at an early stage in the infectious process since immune compromised individuals generally seek medical attention earlier than those not immunocompromised. Furthermore, it is suspected that at least some of the urinary profile is due to the immune response. In this regard, a compromised immune system could result in changes to the metabolic profile, and it is possible that these metabolites are always low for cases of immunocompromised individuals with *S. pneumoniae* pneumonia. Although this may be possible, the results indicate a high accuracy rate (91%) for this diagnostic approach.

The fact that disease states in each of humans and mice caused by lung infection with *S. pneumoniae* produced similar urinary metabolic profiles is not unexpected. Both creatine and taurine were found to increase in infected human and mouse urine, while citrate and succinate decreased. Interestingly, changes in metabolite profiles of lung epithelial cell culture supernatants upon incubation with *S. pneumoniae* showed some resemblance to urinary profiles of *S. pneumoniae* infected patients. Increases in alanine, serine, threonine, acetate, lactate and acetone were found in both infected human urine and cell culture supernatants, while glycine was observed to decrease. An interesting similarity across all samples was the universal decrease in glycine, suggesting that this metabolite is similarly affected across species and cellular events by *S. pneumoniae* infection.

Without wishing to be bound by theory, it is believed that metabolic changes resulting from pneumococcal infection are likely related to cellular events, such as altered mitochondrial activity, energy metabolism, and amino acid transport. The interplay between host and pathogen is particularly complex, involving not only the bacterium and its virulence, but the immune response as well. Since the findings in cell cultures showed that extracellular nutrients, such as glucose, were not completely depleted, it stands to reason that the metabolic changes observed under these conditions were unrelated to nutrient exhaustion, and may instead be related to receptor activation, host cell invasion, and cell lysis caused by *S. pneumoniae*-derived pneumolysin. Indeed, pneumolysin has been shown to introduce pores in cell and mitochondrial membranes, thereby causing leakage and altering mitochondrial membrane potential[16]. Variations in TCA cycle intermediates may be solely attributable to the host response, since *S. pneumoniae* lacks genes expressing enzymes required for the TCA cycle, and therefore is unable to generate TCA cycle intermediates[17]. Other changes are likely related to inflammation and potentially sepsis[18].

While this invention has been described with reference to illustrative embodiments and examples, the description is not intended to be construed in a limiting sense. Thus, various modification of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

References 1. Cunha, B. A. Community-acquired pneumonia. Diagnostic and therapeutic approach. *Med Clin North Am* 85, 43-77 (2001).
2. Marrie, T., Campbell, G., Walker, D. & Low, D. *Pneumonia*, (McGraw-Hill, Medical Publishing Division, 2005).
3. Cunha, B. A. Nosocomial pneumonia diagnostic and therapeutic considerations. *Med Clin North Am* 85, 79-114 (2001).
4. Brandenburg, J. A., et al. Clinical presentation, processes and outcomes of care for patients with pneumococcal pneumonia. *J Gen Intern Med* 15, 638-646 (2000).
5. Fine, M. J., et al. Prognosis and outcomes of patients with community-acquired pneumonia. A meta-analysis. *JAMA* 275, 134-141 (1996).
6. Wilson, P. A. & Ferguson, J. Severe community-acquired pneumonia: an Australian perspective. *Int Med J* 35, 699-705 (2005).
7. Ridgway, E. J., Tremlett, C. H. & Allen, K. D. Capsular serotypes and antibiotic sensitivity of *Streptococcus pneumoniae* isolated from primary-school children. *J Infect* 30, 245-251 (1995).
8. Musher, D. M. Infections caused by *Streptococcus pneumoniae*: clinical spectrum, pathogenesis, immunity, and treatment. *Clin Infect Dis* 14, 801-807 (1992).
9. Marston, B. J., et al. Incidence of community-acquired pneumonia requiring hospitalization. Results of a population-based active surveillance study in Ohio. The community-based pneumonia incidence study group. *Arch Intern Med* 157, 1709-1718 (1997).
10. Centers for Disease Control and Prevention. Defining the public health impact of the drug-resistant *Streptococcus pneumoniae*: report of a working group. *MMWR Morbid Mortal Weekly Rep* 45(RR-1), 1-21 (1996).
11. Stulbarg, M. Problems in diagnosing pneumonia, *West J Med* 140, 594-601 (1984).
12. Faden, H., Heimerl, M., Varma, C., Goodman, G. & Winkelstein, P. Urinary excretion of pneumococcal cell wall polysaccharide in children. *Pediatr Infect Dis J* 21, 791-793 (2002).
13. Lindon, J. C., Holmes, B., Bollard, M. E., Stanley, E. G. & Nicholson, J. K. Metabonomics technologies and their applications in physiological monitoring, drug safety assessment and disease diagnosis. *Biomarkers* 9, 1-31 (2004).
14. Lindon, Holmes, E. & Nicholson, J. K. So what's the deal with metabonomics? *Anal Chem* 75, 384A-391A (2003).
15. Oresic, M., Vidal-Puig, A. & Hamden, V. Metabolomic approaches to phenotype characterization and applications to complex diseases. *Expert Rev Mol Map* 6, 575-585 (2006).
16. Braun, J. S., et al. Pneumolysin causes neuronal cell death through mitochondrial damage. *Infect Immun* 75, 4245-4254 (2007).
17. Hoskins, J., et al. Genome of the bacterium *Streptococcus pneumoniae* Strain R6. *J Bact* 183, 5709-5717 (2001).
18. Leverve, X. M. Mitochondrial function and substrate availability. *Crit Care Med* 35, S454-S460 (2007).
19. Slupaky, C. M., at al. Investigations of the effects of gender, diurnal variation, and age in human urinary metabolomic profiles. *Anal Chem* 79, 6995-7004 (2007).

Supplementary Methods

Mice: Mice were housed and handled according to approved protocols of the HSAPWC, and kept under artificial light on a 12:12-h light/dark cycle for 1 week prior to infection. Mice had access to water and food ad libitum. Mice were subjected to inhalation narcosis with 4% isoflurane and 96% oxygen with a flow rate of 0.5 L/min. Once anaesthetized, mice were infected by injection of either 40 µL THB, or 40 µL *S. pneumoniae* serotype 14 ($30 \times 10^6$ cfu) in THB between the second and third tracheal cartilages, directed toward the bifurcation of the trachea. Skin was sutured after surgery. After mice revived from surgery, they were placed into pre-labeled cages and monitored every six hours to determine health status and signs of disease, and evaluated according to animal care criteria. At 24 hours, mice were sacrificed by overdose with ketamine/rompun. Blood was obtained by cardiac puncture, and serum was collected. Serum was stored at −80° C. until preparation for analysis. Urine was obtained by puncturing the base of the bladder with a syringe. Bronchoalveolar lavage (BAL) samples were obtained by accessing the mouse trachea as described above, and injecting 1 mL of ice-cold Hank's Balanced Salt Solution (HESS) into the lungs. BAL fluid was collected during massage of the chest. HAL samples were centrifuged at 14,000×g at 4° C. for 10 min to pellet cells and bacteria. Supernatants were snap frozen and stored at −80° C.

For longitudinal studies, spot urine samples were collected at specific time intervals by placing mice over weigh-boats, allowing them to urinate, and measuring urine volume prior to analysis.

Lungs for histology were fixed with formalin, embedded in paraffin wax, sectioned, stained with hematoxylin eosin stain (H/E), evaluated for the presence of severity of inflammation, and photographed.

Cell Culture. Human bronchial epithelial A549 cells were cultured in Corning 6-well plates in complete DMEM (Dulbecco-modified Eagle media) growth media supplemented with non-essential amino acids (NEAA), 2 mM L-glutamine and 10% fetal bovine serum (FBS) purchased from Invitrogen, Carlsbad, Calif., USA. At 80-90% confluence ($\sim 10^6$ A549 cells), media was removed, washed four times with HESS and changed to 2 mL of serum-free DMEM (with L-glutamine and NEAA), Control plates (n=3) contained serum-free DMEM as described above. All plates were pre-incubated for 2 hours at 37° C. and 5% $CO_2$. *S. pneumoniae* serotype 14 was cultured as described above, washed three times with DMEM, and diluted to concentrations of $10^1$, $10^1$, $10^3$, $10^4$ and $10^5$ cfu/100 µL. 100 µL of each suspension was added to wells 2 to 6 on each plate. Plates were incubated for 24 hours, and supernatants collected and snap frozen at −80° C. for further analysis.

What is claimed is:

1. A method of diagnosing a disease state in a subject, wherein the disease state is caused or effected by a pneumococcal infection, comprising:
   (a) obtaining a plurality of diseased biological test samples known to have the disease state, wherein the biological test samples include metabolites selected from the group consisting of citrate, trigonelline, acetylcarnitine, acetone, myo-inositol, 3-hydroxybutyrate, glucose and carnitine;
   (b) for each diseased biological test sample, discretely identifying more than one metabolite from said metabolites in the biological test sample and determining a respective concentration of each of the discretely identified metabolites;
   (c) generating a predetermined profile of the disease state using at least the respective concentration of the identified metabolites, the predetermined profile comprising a plurality of data sets;

(d) obtaining a biological test sample from the subject, discretely identifying said more than one metabolite in the biological test sample, determining a respective concentration of each of the identified metabolites in the biological test sample, and determining a test profile using at least the respective concentration of the identified metabolites in the biological test sample; and (e) using multivariate statistical analysis, comparing the test profile of the biological test sample from the subject with the predetermined profile of the disease state to determine a probability of the biological test sample having the disease state.

2. The method as claimed in claim 1, wherein the comparing is effected to provide a diagnosis of the disease state in the subject.

3. The method as claimed in claim 1, wherein the disease state is caused by *streptococcus pneumoniae*.

4. The method as claimed in claim 1, wherein the biological test sample is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, and urine.

5. The method as claimed in claim 1, wherein the biological test sample is urine.

6. The method as claimed in claim 1, wherein the multivariate statistical analysis is selected from the group consisting of principal component analysis, discriminant analysis, principal component analysis with discriminant analysis, partial least squares, partial least squares with discriminant analysis, canonical correlation, kernel principal component analysis, non-linear principal component analysis, factor analysis, multidimensional scaling, and cluster analysis.

7. The method as claimed in claim 1, wherein each one of the biological test sample profile and the predetermined profile is information derived from a respective region of a score plot using multivariate statistical analysis.

8. The method as claimed in claim 1, wherein the respective concentration of each of the identified metabolites is determined using a spectrometric technique, wherein the spectrometric technique is any one of liquid chromatography, gas chromatography, liquid chromatography-mass spectrometry, gas chromatography-mass spectrometry, high performance liquid chromatography-mass spectrometry, capillary electrophoresis-mass spectrometry, nuclear magnetic resonance spectrometry, raman spectroscopy, and infrared spectroscopy.

9. The method as claimed in claim 1, wherein the respective concentration of the identified metabolites is determined using nuclear magnetic resonance spectrometry (NMR).

10. The method of claim 9, wherein determining the respective concentration of a metabolite comprises obtaining a NMR spectrum of the biological sample and comparing the NMR spectrum to a library of known compounds.

11. The method of claim 1, further comprising the steps of:
obtaining a plurality of non-diseased biological test samples known to be free of the disease state, wherein the non-diseased biological samples include more than one metabolite selected from the group consisting of citrate, trigonelline, acetylcarnitine, acetone, myo-inositol, 3-hydroxybutyrate, glucose and carnitine; and
for each non-diseased biological sample, identifying more than one metabolite of the metabolites included in the non-diseased biological test samples, and determining a respective concentration of each of the identified metabolites;

wherein generating a predetermined profile of the disease state further comprises comparing the respective concentration of the identified metabolites in the diseased biological test samples and the non-diseased biological test samples.

12. A method of diagnosing a disease state in a subject, wherein the disease state is caused or effected by a pneumococcal infection, comprising:

(a) generating a predetermined profile of the disease state by obtaining a plurality of diseased biological test samples known to have the disease state, discretely identifying more than one metabolite in the diseased test samples, and measuring a respective concentration of each of the identified more than one metabolite, wherein the more than one identified metabolite is selected from the group consisting of citrate, trigonelline, acetylcarnitine, acetone, myo-inositol, 3-hydroxybutyrate, glucose and carnitine in each diseased biological test sample;

(b) obtaining a biological test sample from the subject, discretely identifying said more than one metabolite in the biological test sample, determining a respective concentration of each of the identified metabolites, and determining a test profile of the biological test sample using at least the respective concentration of the identified metabolites in the biological test sample; and (c) using multivariate statistical analysis, comparing a respective concentration of the identified metabolites in the biological test sample with the predetermined profile of the disease state to determine a probability of the biological test sample having the disease state.

13. The method as claimed in claim 12, wherein the comparing is effected to provide a diagnosis of the disease state in the subject.

14. The method as claimed in claim 12, wherein the pneumococcal infection is *streptococcus pneumoniae*.

15. The method as claimed in claim 12, wherein the biological test sample is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, urine, tissue, sputum.

16. The method as claimed in claim 12, wherein the biological test sample is urine.

17. The method as claimed in claim 12, wherein the respective concentration of each of the identified metabolites is determined using a spectrometric technique, wherein the spectrometric technique is any one of liquid chromatography, gas chromatography, liquid chromatography-mass spectrometry, gas chromatography-mass spectrometry, high performance liquid chromatography-mass spectrometry, capillary electrophoresis-mass spectrometry, and nuclear magnetic resonance spectrometry, raman spectroscopy, and infrared spectroscopy.

18. The method as claimed in claim 12, wherein the respective concentration of each of the identified metabolites is determined using nuclear magnetic resonance spectrometry (NMR).

19. The method of claim 18, wherein determining the respective concentration of a metabolite comprises obtaining a NMR spectrum of the biological sample and comparing the NMR spectrum to a library of known compounds.

20. The method of claim 12, wherein generating a predetermined profile of a disease state further comprises obtaining a plurality of non-diseased biological test samples known to be free of the disease state and identifying and measuring a respective concentration of each of the more than one metabolite in the non-diseased biological test samples.

21. The method of claim 20, wherein generating a predetermined profile of the disease state further comprises comparing the respective concentration of the identified metabolites in the diseased biological test samples and the non-diseased biological test samples.

22. A method of diagnosing a disease state in a subject, wherein the disease state is caused or effected by a pneumococcal infection, comprising:
  (a) obtaining a biological test sample from the subject, wherein the biological sample includes metabolites selected from the group consisting of citrate, succinate, lmethylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, 3-hydroxybutyrate, acetone, carnitine, acetylcarnitine, hypoxanthine, fucose, myo-inositol, taurine, creatine, 2-oxoglutarate and fumarate;
  (b) discretely identifying more than one metabolite from said metabolites in the biological sample and determining a respective concentration of each of the identified metabolites;
  (c) determining a profile for the biological test sample using at least the respective concentration of each of the identified metabolites; and
  (d) using multivariate statistical analysis, comparing the profile of the biological test sample with a predetermined profile indicative of the disease state to determine a probability of the biological test sample having the disease state, the predetermined profile being obtained by profiling a plurality of biological samples known to have the disease state by discretely identifying said more than one metabolite in the diseased samples and determining a respective concentration of each of the identified metabolites in the diseased samples.

23. The method of claim 22, wherein the comparing is effected to provide a diagnosis of the disease state in the subject.

24. The method of claim 22, wherein the disease state is caused by streptococcus pneumoniae.

25. The method of claim 22, wherein the biological test sample is one of blood, blood plasma, blood serum, cerebrospinal fluid, bile acid, saliva, synovial fluid, pleural fluid, pericardial fluid, peritoneal fluid, feces, nasal fluid, ocular fluid, intracellular fluid, intercellular fluid, lymph fluid, and urine.

26. The method of claim 22, wherein the biological test sample is urine.

27. The method of claim 22, wherein the multivariate statistical analysis is selected from the group consisting of principal component analysis, discriminant analysis, principal component analysis with discriminant analysis, partial least squares, partial least squares with discriminant analysis, canonical correlation, kernel principal component analysis, non-linear principal component analysis, factor analysis, multidimensional scaling, and cluster analysis.

28. The method of claim 22, wherein each one of the biological test sample profile and the predetermined profile is information derived from a respective region of a score plot using multivariate statistical analysis.

29. The method of claim 22, wherein the respective concentration of each of the identified metabolites is determined using a spectrometric technique, wherein the spectrometric technique is any one of liquid chromatography, gas chromatography, liquid chromatography-mass spectrometry, gas chromatography-mass spectrometry, high performance liquid chromatography-mass spectrometry, capillary electrophoresis-mass spectrometry, nuclear magnetic resonance spectrometry, raman spectroscopy, and infrared spectroscopy.

30. The method of claim 22, wherein the respective concentration of the identified metabolites is determined using nuclear magnetic resonance spectrometry (NMR).

31. The method of claim 30, wherein determining the respective concentration of a metabolite comprises obtaining a NMR spectrum of the biological sample and comparing the NMR spectrum to a library of known compounds.

32. The method of claim 22, further comprising the steps of:
  obtaining a plurality of non-diseased biological test samples known to be free of the disease state, wherein the non-diseased biological samples include more than one metabolite selected from the group consisting of citrate, succinate, lmethylnicotinamide, levoglucosan, trigonelline, hippurate, glycine, ethanolamine, uracil, dimethylglycine, guanidoacetate, glycolate, π-methylhistidine, alanine, asparagine, isoleucine, leucine, lysine, serine, threonine, tryptophan, tyrosine, valine, glucose, acetate, lactate, 3-hydroxybutyrate, acetone, carnitine, acetylcarnitine, hypoxanthine, fucose, myo-inositol, taurine, creatine, 2-oxoglutarate and fumarate; and
  for each non-diseased biological sample, identifying more than one metabolite of the metabolites included in the non-diseased biological test samples, and determining a respective concentration of each of the identified metabolites;
  wherein generating a predetermined profile of the disease state further comprises comparing the respective concentration of the identified metabolites in the diseased biological test samples and the non-diseased biological test samples.

* * * * *